United States Patent
Patarin

(10) Patent No.: US 12,135,267 B2
(45) Date of Patent: Nov. 5, 2024

(54) IN VITRO METHOD FOR DIAGNOSING, STRATIFYING, PROGNOSING AND/OR MONITORING A LUNG DISEASE AND/OR A RESPIRATORY DISEASE

(71) Applicant: RHEONOVA, Grenoble (FR)

(72) Inventor: Jérémy Patarin, Revel (FR)

(73) Assignee: RHEONOVA, Grenoble (FR)

( * ) Notice: Subject to any disclaimer, the term of this patent is extended or adjusted under 35 U.S.C. 154(b) by 13 days.

(21) Appl. No.: 17/598,791

(22) PCT Filed: Mar. 30, 2020

(86) PCT No.: PCT/EP2020/058982
§ 371 (c)(1),
(2) Date: Sep. 27, 2021

(87) PCT Pub. No.: WO2020/193811
PCT Pub. Date: Oct. 1, 2020

(65) Prior Publication Data
US 2022/0170836 A1    Jun. 2, 2022

(30) Foreign Application Priority Data
Mar. 28, 2019    (FR) ...................................... 1903302

(51) Int. Cl.
*G01N 33/487*    (2006.01)
*G01N 11/14*    (2006.01)

(52) U.S. Cl.
CPC ......... *G01N 11/142* (2013.01); *G01N 33/487* (2013.01)

(58) Field of Classification Search
CPC ........................... G01N 11/142; G01N 33/487
(Continued)

(56) References Cited

FOREIGN PATENT DOCUMENTS

WO    WO-2011/121462 A1    10/2011
WO    WO-2019122785 A1    6/2019

OTHER PUBLICATIONS

International Search Report and Written Opinion for Corresponding International Application No. PCT/EP2020/058982 mailing date Jun. 26, 2020.
(Continued)

*Primary Examiner* — Robert R Raevis
(74) *Attorney, Agent, or Firm* — MARSHALL, GERSTEIN & BORUN LLP

(57) ABSTRACT

An in vitro method for diagnosing, stratifying, prognosing and/or monitoring a lung and/or respiratory disease, and for evaluating the effectiveness of a treatment of a lung and/or respiratory disease, can include the determination or the measurement of the value $A_{nl}$ of at least one rheological parameter on a sample of mucus A of a subject, in a non-linear zone of the deformation curve of the sample, and/or of the value $A_l$ of at least one rheological parameter on said sample, in a linear zone of the deformation curve of the sample, wherein the rheological parameter is selected from the elasticity modulus (G'), the viscosity modulus (G"), the complex modulus G*, the damping factor (tan δ), the complex modulus (G*), the critical deformation ($\gamma_c$), the plastic deformation ($\gamma_p$), the flow stress threshold ($\tau_c$), the plastic stress ($\tau_p$), and the elastic force (EF), the critical stress ($\sigma_c$), and any combination thereof.

21 Claims, 7 Drawing Sheets

(58) Field of Classification Search
USPC ......... 73/54.01, 54.02–54.43, 760, 788–793,
73/826–830, 865.9; 600/529–542
See application file for complete search history.

(56) References Cited

OTHER PUBLICATIONS

The Global Impact of Respiratory Diseases, Second Edition, Forum of International Respiratory Societies, 2017.

Ma et al., Chest, Cystic fibrosis sputum rheology correlates with both acute and longitudinal changes in lung function, Manuscript (2018).

Nettle et al., Linear rheology as a potential monitoring tool for sputum in patients with Chronic Obstructive Pulmonary Disease (COPD): Biorheology, 54(2-4), 2017,67-80.

Patarin et al., Change of mucus rheology in patients with Cystic Fibrosis, COPD and Asthma: European respiratory journal, 52(62), 2018, PA5051.

Serisier et al., "Macrorheology of cystic fibrosis, chronic obstructive pulmonary disease & normal sputum" Respiratory research, 10(1), 2009, 63.

Tomaiulo et al., A new Method to improve the Clinical Evaluation of Cystic Fibrosis patients by Mucus, Viscoelastic Properties. Plos One, 9(1), 2014, e82297, pp. 1-13.

"Understanding Yield Stress Measurements", Aug. 4, 2015 (Aug. 4, 2015), Retrieved from the Internet: URL:https://cdn.technologynetworks.com/TN/Resources/PDF/WP120416UnderstandYieldStressMeas.pdf XP055705127.

IN VITRO METHOD FOR DIAGNOSING, STRATIFYING, PROGNOSING AND/OR MONITORING A LUNG DISEASE AND/OR A RESPIRATORY DISEASE

CROSS REFERENCE TO RELATED APPLICATIONS

This application is a U.S. National Stage of International Patent Application No. PCT/EP2020/058982 filed Mar. 30, 2020, which claims the benefit of priority of French Patent Application No. 1903302 filed Mar. 28, 2019, the respective disclosures of which are each incorporated herein by reference in their entireties.

FIELD OF THE INVENTION

The present invention lies in the field of the diagnosis and the monitoring of lung diseases and/or respiratory diseases. It relates to an in vitro method for diagnosing, stratifying, prognosing and/or monitoring a lung disease and/or a respiratory disease, comprising the determination or the measurement of at least one rheological parameter on a sample of mucus/expectoration of a subject, in the non-linear zone of the deformation curve of the sample and/or at least one rheological parameter in the linear zone of said curve. The present invention also relates to an in vitro method for evaluating the effectiveness of a treatment of a lung disease and/or a respiratory disease, based on the determination or the measurement of said parameters.

PRIOR ART

The respiratory apparatus is constituted of organs particularly sensitive to infections and to traumas (in particular the lungs), due to their large contact surface and their constant exposure to particles, chemicals and infectious organisms present in the ambient air.

Respiratory diseases and lung diseases are diseases that are able to have serious consequences and cause numerous deaths in all regions of the globe.

They are however often undiagnosed or may be diagnosed late, when the disease is at an advanced stage and more difficult to treat.

According to a report published by the World Health Organisation (WHO) in 2017, the estimations put at 65 million the number of persons suffering from chronic obstructive pulmonary disease (COPD) worldwide, a disease that causes 3 million deaths a year. Around 334 million people in the world are asthmatic, with an endlessly increasing prevalence in children, while millions of others suffer from allergic rhinitis and other chronic respiratory diseases, rarely diagnosed and sometimes mortal (The Global Impact of Respiratory Diseases, Second Edition, Forum of International Respiratory Societies, 2017).

The main symptoms leading to a search for respiratory diseases or lung diseases are difficulty in breathing and abnormal expectoration.

The tools for diagnosing and monitoring patients notably comprise functional respiratory effort tests (consisting in measuring the capacity of the lungs to retain and displace air and to exchange oxygen and carbon dioxide), microbiological analyses of expectorations, imaging examinations, bronchoscopy and thoracoscopy.

However, these methods are not very suitable for an early diagnosis and the discrimination of the different diseases or their stage of evolution (stratification) remains difficult and totally empirical, which may lead to unsuitable or too late treatments.

Expectoration is an essential factor of the normal clearance of the respiratory tracts and the pulmonary function. Mucus is found in the upper airways where a protective layer of the epithelium forms. Mucus helps to maintain the homeostasis of the respiratory tracts by aiding the elimination of pathogenic agents and foreign particles. An equilibrium in the production of mucus and clearance is essential for the health of the respiratory tracts and changes in the viscoelastic properties can greatly affect this process.

The viscoelastic properties of the mucus have been studied in patients suffering from chronic obstructive pulmonary disease (COPD) or cystic fibrosis, on the basis of elasticity (G') and viscosity (G") moduli. Different studies suggest that these viscoelastic properties evolve as a function of the stage of the disease, in patients suffering from COPD or cystic fibrosis (Serisier et al., 2009; WO2011/121462; Tomaiuolo et al., 2014; Nettle et al., 2017; Ma et al., 2018). However, the data have not made it possible to discriminate these different respiratory diseases in a statistical manner. Further, the measurements are carried out in quasi-static operating conditions which are not representative of the mucus in physiological conditions. Hence, these measurements remain not very reliable and do not make it possible to analyse or to predict finely enough the condition of the patient.

There thus exists a need to develop new diagnostic tests for respiratory diseases and lung diseases, based on measurements of the rheological properties of the mucus in physiological conditions, thus enabling the reliable prediction of the condition of the patient, in order to favour earlier care as well as the putting into practice of targeted treatments.

The present invention makes it possible to meet this need. The present Inventors have conducted three clinical studies having made it possible to demonstrate for the first time that the rheological parameters of the mucus of patients with different respiratory diseases are statistically different from one disease to the other, thus making it possible to distinguish different respiratory and pulmonary diseases. The Inventors have notably shown that these rheological parameters may be used as biomarkers and make it possible to discriminate respiratory diseases both when they are measured in the linear zone of the deformation curve of the mucus and when they are measured in the non-linear zone of this curve. The data show that the combination of the determination or the measurement of a rheological parameter in the linear zone with the determination or the measurement of a rheological parameter (identical or different) in the non-linear zone of the deformation curve of the mucus enables a particularly reliable, efficient and significant discrimination. In addition, the data show that the prior treatment of patients with rhDNase (recombinant human deoxyribonuclease) has an effect on the rheological parameters of the mucus of the patient, thus revealing for the first time that the measurement of rheological parameters makes it possible to evaluate the mucolytic effect of a treatment.

The data obtained by the inventors are all the more relevant when they have been obtained using a device developed by the Inventors, making it possible to simulate the flow of mucus in physiological situation. The Inventors have notably shown that this device makes it possible to obtain in a reproducible manner measurements of viscoelastic and rheological properties of the mucus placed in physiological conditions. The Inventors have thus developed a novel method enabling reliable diagnosis, stratification, prognosis and monitoring of lung diseases and other respiratory diseases, based on the measurement of rheological parameters in the linear zone of the deformation curve and rheological parameters in the non-linear zone of this curve obtained from the mucus of patients. The Inventors have also developed a novel method for evaluating the effectiveness of a treatment of lung diseases and respiratory diseases, based on the measurement of these parameters.

This invention also provides novel diagnostic tests, such as companion tests, enabling the reliable prediction of the condition of the patient and the putting into practice of targeted treatments.

DESCRIPTION OF THE INVENTION

Within the scope of the present invention, the Inventors have demonstrated, in an entirely surprising manner, that the determination or the measurement of a combination of rheological parameters on the mucus of patients, both in the linear zone and in the non-linear zone of the deformation curve of the mucus, makes it possible to distinguish different pulmonary and/or respiratory diseases.

The present invention thus relates to a novel in vitro method for diagnosing, stratifying, prognosing and/or monitoring a lung disease and/or a respiratory disease comprising the determination or the measurement of such rheological parameters. The invention also relates to a novel in vitro method for evaluating the effectiveness of a treatment of a lung disease and/or a respiratory disease, comprising the determination or the measurement of such rheological parameters.

The present invention also relates to the use of such rheological parameters for diagnosing, stratifying, prognosing and/or monitoring a lung disease and/or a respiratory disease; and/or for evaluating the effectiveness of a treatment of a lung disease and/or a respiratory disease.

The present invention also relates to a companion test, using such rheological parameters for diagnosing, stratifying, prognosing and/or monitoring a lung disease and/or a respiratory disease; and/or for evaluating the effectiveness of a treatment of a lung disease and/or a respiratory disease.

DETAILED DESCRIPTION OF THE INVENTION

Definitions

Figure 1:
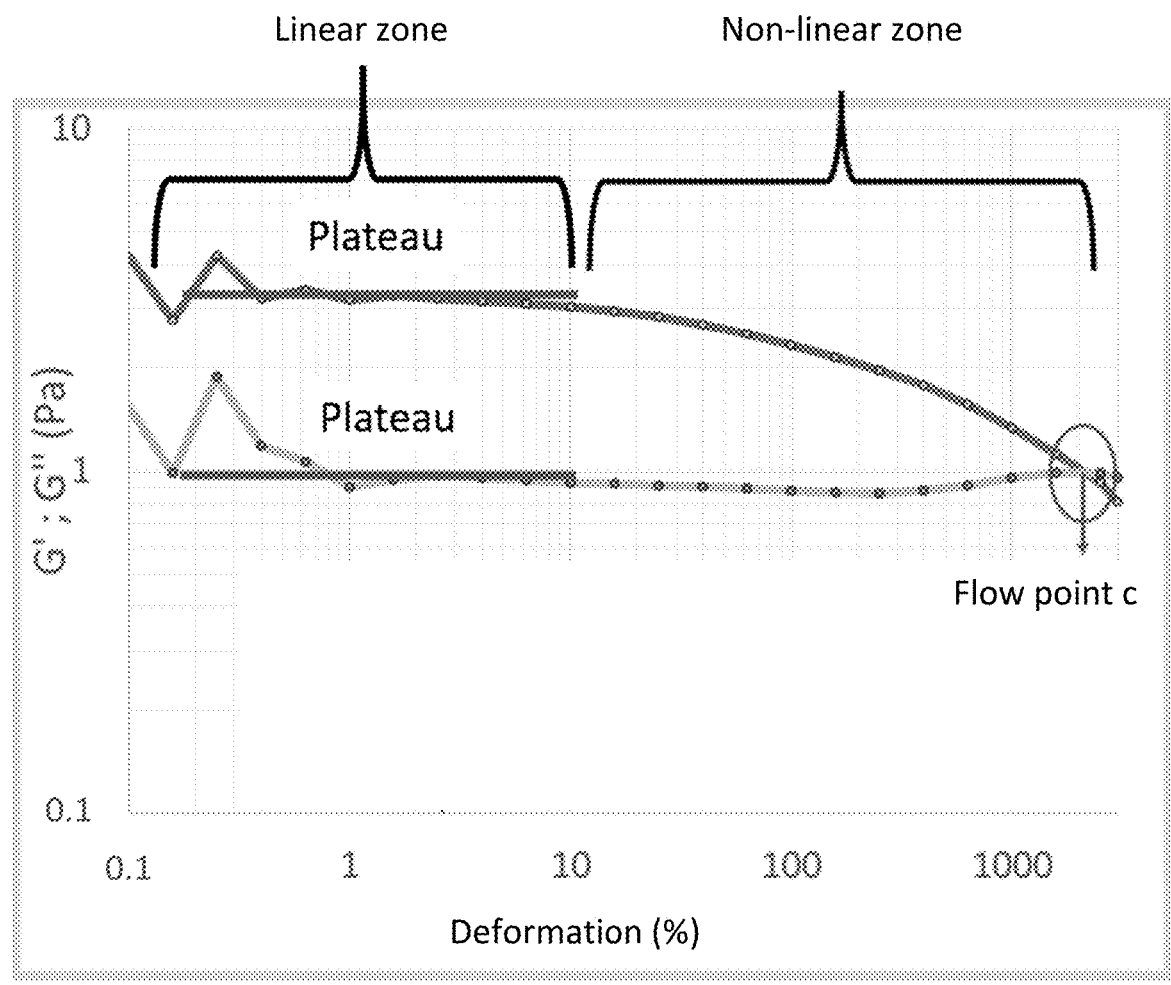
FIG. 1 shows a typical example of deformation curve and shows the linear zone, which comprises a plateau, and the non-linear zone.

"Diagnosis" herein refers to the identification/determination of a disease, or the absence of a disease, in a subject. Diagnosis comprises for example the search for the causes (aetiology) and the effects (symptoms) of the disease, notably on the basis of observations and/or measurements, carried out using different tools. In the case of respiratory and/or pulmonary diseases, the diagnostic tools comprise respiratory functional effort tests (consisting in measuring the capacity of the lungs to retain and displace air and to exchange oxygen and carbon dioxide), microbiological analyses of expectorations, imaging examinations, bronchoscopy and thoracoscopy.

"Stratification" herein refers to the separation/classification of subjects into sub-groups by severity/seriousness of the disease. The different sub-groups notably comprise the sub-group of healthy subjects as well as different sub-groups of subjects suffering from a disease, classed as a function of the stage of evolution/advancement of the disease. The evolution stage may be determined on the basis of observations and/or measurements, carried out using different tools. In the case of respiratory and/or pulmonary diseases, stratification tools comprise the tools that are also used for their diagnosis.

"Prognosis" herein refers to the prediction/determination/ evaluation of the risks of evolution of a disease in a subject. Prognosis notably comprises the evaluation of the future development of the condition of the subject and the potential chances of healing. The prognosis may be determined on the basis of observations and/or measurements, carried out using different tools. In the case of respiratory and/or pulmonary diseases, prognostic tools comprise the tools that are also used for their diagnosis or the stratification of subjects.

"Monitoring" herein refers to the determination/evaluation of the evolution of a disease in a subject. Monitoring may be carried out on the basis of observations and/or measurements, conducted using different tools, at different time intervals. The intervals may be regular or irregular. Their frequency depends on the disease but also the stage of evolution of the disease. It may be of the order of several days (for example in the case of disease at a severe/advanced/serious stage and/or in the case of a rapidly evolving disease and/or in the case of exacerbation phase) to several years (for example in the case of a disease at a preliminary stage, mild or moderate, and/or in the case of a slowly evolving disease). In the case of respiratory and/or pulmonary diseases, the monitoring tools comprise the tools that are also used for the diagnosis or the prognosis of the disease, or the stratification of subjects.

"Evaluation of the effectiveness/efficacy of a treatment" herein refers to the determination of the clinical condition of a subject subjected to a treatment. The treatment may be preventive, for example in the case of predisposition to a disease, or it may be curative, for example in the case of a diagnosed disease. The effectiveness of the treatment may for example be evaluated by determining the condition of the subject at different time intervals. The condition of the subject may notably be evaluated before the first taking of the treatment then at regular (or irregular) time intervals after this first taking (for example after each new taking of the treatment). A comparison of the condition of the subject evaluated at these different intervals may then be carried out in order to identify a potential change. The condition of the patient may be evaluated on the basis of observations and/or measurements, carried out using different tools. In the case of respiratory and/or pulmonary diseases, the tools for evaluating the effectiveness of a treatment comprise the tools that are also used for the diagnosis, the prognosis or the monitoring of the disease, or the stratification of subjects.

"Companion test" herein refers to a diagnostic test making it possible to select, as a function of their status for a marker identified by this test (such as a predictive marker), uniquely patients in whom the treatment is capable of bringing a benefit from among those diagnosed for a given disease. The companion test is for example such as defined by the Haute Autorité de la Santé (French National Authority for Health) (notably such as defined in the Guide Methodologique: Test compagnon associé à une thérapie ciblée: définitions et méthode d'évaluation (Methodological Guide: Companion test associated with a targeted therapy: definitions and evaluation method) published in February 2014. The marker is preferably the value of a rheological parameter, further preferably the value of a rheological parameter determined/measured on a sample of mucus of a subject, said rheological parameter advantageously being such as defined below and/or being determined/measured such as explained below.

"Respiratory disease" herein refers to a disease (or ailment) affecting the respiratory apparatus. The respiratory apparatus is a set of organs enabling respiration (that is to say gaseous exchanges between the organism and the environment). In mammals such as humans, the respiratory apparatus comprises the nose, the mouth, the pharynx, the larynx, the trachea, the diaphragm and the lungs, the latter comprising the bronchial tubes, the bronchioles, the alveolus and the acini. "Lung disease" or "pulmonary disease" herein refers to a respiratory disease that affects the lungs. The respiratory and/or pulmonary diseases may be of infectious, viral, genetic, environmental origin, or result from a combination of these factors. Respiratory diseases and lung diseases comprise for example asbestosis; sleep apnoea; obstructive sleep apnoea syndrome; asphyxia; asthma; bronchiectasis; bronchitis, including acute bronchitis and chronic bronchitis; chronic obstructive pulmonary disease (COPD); lung cancer; bronchial cancer; pulmonary carcinoma; pulmonary tumour; whooping cough; croup; alpha1-antitrypsine deficiency; emphysema; cystic fibrosis; idiopathic pulmonary fibrosis; influenza, including seasonal influenza and influenza A; hantavirus pulmonary syndrome; pulmonary arterial hypertension (PAHT); lymphangioleiomyomatosis (LAM); obstructive chronic pulmonary disease (COPD); pleuritis; pneumonia; bronchopneumonia; pulmonary emboli; pulmonary oedema; pulmonary abscess; cold; sinusitis; sarcoidosis; thoracic trauma; chronic cough; tuberculosis; infection by the respiratory syncytial virus (RSV); bronchiolitis; bronchiolitis obliterans organising pneumonia (BOOP); allergy, in particular respiratory allergy; allergic rhinitis; primary ciliary dyskinesia (PCD); bronchiectasis (BTS); pneumoconiosis; pneumothorax (PNO); pleuritis; cancer of the pleura; legionellosis; psittacosis; preferably said disease is chosen from among BTS, COPD, cystic fibrosis and asthma.

"Stage of a respiratory and/or pulmonary disease", "stage of evolution of a respiratory and/or pulmonary disease" or "stage of advancement of a respiratory and/or pulmonary disease" herein refers to a phase of the respiratory and/or pulmonary disease that is determined according to the seriousness of the symptoms of which the subject suffers and their implications/consequences on the mode and/or the quality of life of the subject. These stages may be four in number. For example:

Stage 1 (or first stage) is called mild disease or mild stage: the patient notably begins to present dyspnoea (shortness of breath on exertion), still limited to important effort, which explains why the patient is often not aware of it and is content to adapt himself by limiting his activities.

Stage 2 (or second stage) can be referred to as moderate disease or moderate stage: shortness of breath becomes present in everyday activities and begins to represent a source of handicap.

Stage 3 (or third stage) can be referred to as severe disease or severe stage: the same symptoms as at stage 2 are found but dyspnoea also occurs for minimum effort in everyday activities.

Stage 4 (or fourth stage) is known as very severe disease or very severe stage: the patient is hindered in the simplest activities (washing or dressing himself) then becomes respiratory insufficient (impossibility of fully ensuring the oxygenation of his organism, which results in cyanosis: more or less marked blueing of the end of the fingers and the lips). The quality of life is, at this stage, considerably altered. In the long run, respiratory insufficiency may be felt on the heart. Oedema of the ankles may appear.

"Exacerbation" or "exacerbation phase" herein refers to a period during which the clinical signs of a respiratory and/or pulmonary disease increase in a subject suffering from said disease. The clinical signs that amplify during exacerbation comprise coughing, expectoration and shortness of breath. Exacerbation may be due to an infection of the bronchial tubes. Exacerbation can take place at all stages of the disease. It is in general not very disturbing during the first stages of the disease but may be more serious when the disease is more advanced. For example, patients monitored for COPD present on average nearly 2 exacerbations a year.

"Subject" or "patient" herein refers to a human individual or an animal different from a human. The subject is for example a human or an animal liable to have a pulmonary and/or respiratory disease or suffering from such a disease. The subject is preferably a human being. The subject may be a child (human subject 16 years old or less) or an adult (human subject more than 16 years old). "Healthy subject" herein refers to a subject who does not suffer from the considered disease. Within the scope of the present invention, a healthy subject is preferably a subject who does not suffer from any respiratory and/or pulmonary disease, further preferably a subject who does not suffer from any disease.

"Mucus" or "expectoration" or "broncho-pulmonary secretion" or "sputum" or "spittle" herein refers to a more or less viscous substance secreted by the mucous glands in humans and animals and serving as protective coating on the surface of the mucous membranes. Expectoration is an essential factor of the normal clearance of the respiratory tracts and of the pulmonary function, which is found in the upper airways where it forms a protective layer of the epithelium. An equilibrium in the production of expectorations and clearance is essential for the health of the respiratory tracts. Expectorations comprise notably high molecular weight glycoproteins, of which mucopolysaccharides for example mucin. The glycoproteins present in the mucus can form a cross-linked polymer structure which determines, at least in part, its viscoelastic behaviour. The mucus may also comprise inflammatory cells, bacteria, filamentous actin and highly polymerised DNA. At the macroscopic level, expectorations may be considered as a non-Newtonian thixotropic gel, which is distinguished by its response to shear stresses.

"Rheological parameter" herein refers to a variable of which the value is measurable, making it possible to qualify the rheological properties of a fluid or a soft solid. These parameters are commonly measured and/or determined using a rheometer.

"Rheological property" herein refers to the deformation and flow properties of a fluid or a soft solid, evaluated under the effect of the stresses that are applied thereto. Deformation properties characterise the manner in which a given material reacts when it is subjected to mechanical stresses. "Flow" corresponds to the overall and irreversible movement of a given material. Rheological properties notably comprise viscosity, elasticity, viscoelasticity and plasticity. These properties are commonly characterised by rheological parameters.

"Viscosity" herein refers to all of the phenomena of resistance to flow occurring in the mass of a material, for a uniform flow and without turbulence. The viscosity of a material reflects its capacity to dissipate energy (for example in the form of heat). The more the viscosity increases, and more the capacity of the fluid to flow easily decreases and the greater will be the energy dissipated by the flow.

"Elasticity" herein refers to the capacity of a material to conserve and to restore energy after deformation. An elastic material deforms instantaneously under the action of an exerted force and recovers its initial shape and size when this force is no longer exerted. A material is generally only elastic up to a certain limit of the value of these forces.

"Viscoelasticity" herein refers to the property of materials that exhibit both viscous and elastic characteristics, when they undergo a deformation. Viscous materials resist shear flow and exhibit deformation which increases linearly with time when a stress is applied.

"Plasticity" herein refers to the property of a material to deform irreversibly. Plastic deformation occurs through a local and irreversible rearrangement of the relative position of the atoms, or more generally the constituent elements, of the material. Under the effect of a stress, a material begins in general by deforming reversibly (elastic deformation), that is to say that its dimensions change and that it recovers its initial shape when the stress stops. So-called fragile materials break in this mode of deformation if the stress is too strong. So-called ductile materials are deformed definitively, from a stress threshold: when the stress is stopped, the material remains deformed.

"Viscoplasticity" herein refers to the inelastic behaviour of a material that depends on the rate of deformation thereof. Dependency on the rate of deformation, in this context, signifies that the deformations are proportional to the loading rate. Inelastic behaviour in the case of viscoplasticity is plastic behaviour which signifies that the material undergoes irreversible deformations when a certain load level is reached.

"Deformation" or "relative deformation" or "□" herein refers to a modification of at least one of the geometric dimensions of a material, relative to the value at rest of said dimension.

"Deformation curve" herein refers to a curve that shows the relationship between the elasticity (represented by the elasticity modulus (G')) and/or the viscosity (represented by the viscosity modulus (G")), for example in Pascal (Pa) units, and the deformation (corresponding to the relative deformation, for example in percentage), for a given material (for example a sample of mucus). A deformation curve generally comprises a linear zone and a non-linear zone. The linear zone generally comprises a plateau zone ("p"). An exemplary deformation curve representing the modules G' and G", typically obtained for a sample of mucus, is given by FIG. 1.

"Linear zone of a deformation curve" or "linear zone", "plateau of a deformation curve" or "plateau" or "flow state" herein refers to the portion of the deformation curve of a given material (for example a sample of mucus) where the stress is proportional to the deformation and the modules G' and G" are constant. In the case of the deformation curve of a sample of mucus, the linear zone is generally situated at a deformation less than or equal to 10% (see the representative example given in FIG. 1), but may also lie at a deformation less than or equal to 5% or instead at a deformation less than or equal to 1%, according to the sample.

"Non-linear zone of a deformation curve" or "non-linear zone" herein refers to the portion of the deformation curve of a given material (for example a sample of mucus) where the stress is a variable function, generally non-linear, of the deformation. In the case of the deformation curve of a sample of mucus, the non-linear zone generally begins at a deformation greater than 10% (see the representative example given in FIG. 1), but may also begin from the moment that the deformation reaches 5% or instead that the deformation reaches 1%, according to the sample.

"Flow point c of a deformation curve" or "flow point" or "modulus crossover" or "c" herein refers to the deformation from which a given material (for example a sample of mucus) begins to flow. The flow point corresponds to the crossover point of the deformation curve representing the elasticity modulus (G') with the deformation curve representing the viscosity modulus (G"), obtained for a given material (see the representative example given in FIG. 1). In general, the flow point "c" of a sample of mucus is reached when the sample of mucus is subjected at a deformation ranging from 400% to 10000%, preferably from 500% to 9000%, preferably from 600% to 8000%, preferably from 700% to 7000%, preferably from 800% to 6000%, preferably from 900% to 5000%, preferably from 1000% to 4000%, further preferably, at a deformation ranging from 500% to 1000%.

"Measurement" or "measurement of a value" or "measurement of a quantity" herein refers to the action of evaluating a quantity (also called value) according to its relationships with a quantity of same kind, taken as unit and as reference, using a measurement apparatus. "Determination" or "determination of a value" or "determination of a quantity" herein refers to the action of evaluating or calculating a quantity (also called value) from a value or a quantity measured using a measurement apparatus.

"Elasticity modulus G'" or "elasticity modulus" or "elastic modulus" or "G'" herein refers to an intrinsic quantity of a material, defined by the ratio of a stress to the elastic deformation caused by this stress. Deformations being dimensionless, elasticity moduli are homogeneous at a pressure and their SI unit is the Pascal (Pa).

"Viscosity modulus G"" or "viscosity modulus" or "viscous modulus" or "G"" herein refers to an intrinsic quantity of a material which characterises its viscous behaviour (notably comprising the energy dissipated, for example in the form of heat). The SI unit of the viscosity modulus is the Pascal (Pa).

"Complex modulus G*" or "complex modulus" or "G*" herein refers to a quantity representative of the general consistency of the material, the value of which is equal to the square root of the sum $G'^2+G''^2$. The SI unit of the complex modulus is the Pascal (Pa).

"Damping factor tan δ", or "damping factor" or "damping ratio" or "tan δ" herein refers to the loss factor. The damping factor correspond to the ratio G"/G' and indicates the weighting between the viscous response and the elastic response of the material under a given mechanical load. The damping factor is a dimensionless quantity.

"Critical deformation $\gamma_c$" or "deformation at flow threshold $\gamma_c$" or "critical deformation" or "deformation at flow threshold" or "$\gamma_c$" herein refers to the relative deformation of a material when it begins to flow. The critical deformation is a dimensionless quantity. It may be expressed in percentage.

"Plastic deformation" or "plastic deformation $\gamma_p$" or "deformation $\gamma_p$" or "plateau deformation" or "$\gamma_p$" herein refers to the value of the stress at the end of the plateau zone of the deformation curve.

"Stress τ" or "stress" or "τ" herein refers to a quantity that characterises the mechanical force applied tangentially (parallel) and/or normally (perpendicular) to a face of a material. The stress corresponds to the ratio of a force to a surface. The SI unit of the stress threshold is the Pascal (Pa).

"Flow stress threshold" or "flow stress threshold $\square_c$" or "$\square_c$" or "stress threshold" herein refers to the value of the stress to exert on the material to make it flow. It is generally obtained from a flow curve. "Plastic stress" or "plastic stress $\tau_p$" or "stress $\tau_p$" or "plateau stress" or "$\tau_p$" herein refers to the value of the stress at the end of the plateau zone of the deformation curve.

"Elastic force EF" or "elastic force" or "EF" herein refers to a quantity of which the value is equal to the product of the elasticity modulus G* measured in the linear zone (plateau) of the deformation curve (parameter also called $G^*_p$) by the stress a measured at the flow point c of the deformation curve (parameter also called $\sigma_c$ or critical stress), according to the formula $EF=G^*_p \sigma_c$. The SI unit of the elastic force is Pascals squared ($Pa^2$).

"Critical stress $\sigma_c$" or "critical stress" or "$\sigma_c$" herein refers to the minimum stress to reach the flow zone, characterised by the rupture of the solid structure at the end of the plastic domain. At this stress level, the viscous contribution becomes greater than the elastic contribution.

"rhDNase" or "human recombinant deoxyribonuclease" herein refers to an enzyme of human origin, catalysing the hydrolysis (breakage) of desoxyribonucleic acids (or DNA) into nucleotides or polynucleotides. It hydrolyses phosphodiester bonds. rhDNase is notably used as medicine having the action of an expectorant in patients suffering from respiratory and/or pulmonary diseases. rhDNase is generally administered to the patient in the form of aerosols, by nebulisation, with the aim of treating bronchial congestion. Treatment by rhDNase aims to improve the respiratory function of patients and to reduce the number of exacerbations. Treatment with rhDNase modifies the rheology of the mucus via an action on the DNA contained in the secretions. Medicines based on rhDNase are known and commercially available (they comprise for example Pulmozyme® (Dornase alfa or rhDNase, Roche).

"Limit value" or "threshold value" or "reference value" herein refers to the value of a rheological parameter indicating the condition of a subject with regard to a respiratory and/or pulmonary disease. According to the context, this value corresponds to the value of a rheological parameter determined or measured on a sample of mucus of a healthy reference subject; or to the average of the values of a rheological parameter determined or measured on different samples of mucus from a same healthy reference subject (values determined/measured on samples of mucus taken at separate time intervals on the same reference subject or values determined/measured on the same sample of mucus at separate time intervals) or to the average of the values of a rheological parameter determined/measured on the mucus of several healthy reference subjects (at least two healthy reference subjects); or to the value of a rheological parameter determined/measured on a sample of mucus of a reference subject at a known stage of the lung disease and/or the respiratory disease; or to the average of the values of a rheological parameter determined/measured on different samples of mucus from a same reference subject at a known stage of the lung disease and/or the respiratory disease (values determined/measured on samples of mucus taken at separate time intervals on the same reference subject or values determined/measured on the same sample of mucus at separate time intervals) or to the average of the values of a rheological parameter determined/measured on the mucus of several reference subjects at a known stage of the lung disease and/or the respiratory disease (at least two reference subjects at a known stage of the lung disease and/or the respiratory disease).

Methods for Diagnosing, Stratifying, Prognosing, Monitoring, Evaluating the Effectiveness of a Treatment Three clinical studies conducted by the Inventors have made it possible to demonstrate for the first time that the rheological parameters of the mucus of patients with different respiratory diseases are statistically different from one disease to the other. The Inventors have notably shown that these rheological parameters may be used as biomarkers making it possible to differentiate respiratory diseases both when they are measured in the linear zone of the deformation curve of the mucus and when they are measured in the non-linear zone of this curve. The data show that the combination of the measurement of a rheological parameter in the linear zone with the measurement of a rheological parameter (identical or different) in the linear zone of the deformation curve of the mucus enables a discrimination that is particularly precise, efficient and significant of these diseases. The Inventors have thus shown that it is possible to diagnose, stratify, prognose or monitor in a reliable and precise manner a lung disease and/or a respiratory disease in a subject, on the basis of the measurement of these parameters. It is also possible to evaluate the effectiveness of a treatment administered to a subject suffering or liable to suffer from such a disease. The Inventors have thus developed a novel method enabling a reliable diagnosis, stratification, prognosis and monitoring of lung diseases and respiratory diseases, based on the measurement of rheological parameters in the linear zone of the deformation curve and rheological parameters in the non-linear zone of this curve obtained from the mucus of patients.

The present invention thus relates to an in vitro method for diagnosing, stratifying, prognosing and/or monitoring a lung disease and/or a respiratory disease, comprising:
  (i) the determination or the measurement of the value $A_{nl}$ of at least one rheological parameter on a sample of mucus A of a subject, in a non-linear zone of the deformation curve of the sample; and/or
  (ii) the determination or the measurement of the value $A_l$ of at least one rheological parameter on said sample of mucus A, in a linear zone of the deformation curve of the sample;
wherein the rheological parameter is chosen from:
  the elasticity modulus (G'),
  the viscosity modulus (G"),
  the damping factor (tan δ),
  the complex modulus (G*),
  the plastic deformation ($\gamma_p$),
  the critical deformation ($\gamma_c$),
  the plastic stress ($\tau_p$),
  the flow stress threshold ($\tau_c$),
  the elastic force (EF),
  the critical stress ($\sigma_c$), and
  any combination thereof;
the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof, further preferably from among $\tau_c$, $\sigma_c$, and any combination thereof, further preferably, the determination of the value $A_{nl}$ comprises at least the determination of the value of the rheological parameter $\sigma_c$;
the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof, further preferably, the determination of the value $A_l$ comprises at least the determination of the value of the rheological parameter G*.

Preferably, the in vitro method for diagnosing, stratifying, prognosing and/or monitoring a lung disease and/or a respiratory disease, comprises at least the determination or the measurement of a rheological parameter chosen from $\sigma_c$*. Advantageously, the determination or the measurement of the value $A_{nl}$ of at least one rheological parameter on a sample of mucus A of a subject, in a non-linear zone of the deformation curve of the sample, comprises at least the determination or the measurement of the value $A_{nl}$ of the rheological parameter $\sigma_c$. Alternatively or in combination, the determination or the measurement of the value $A_l$ of at least one rheological parameter on a sample of mucus A of a subject, in a linear zone of the deformation curve of the sample, comprises at least the determination or the measurement of the value $A_l$ of the rheological parameter G*. Preferably, the rheological parameter determined or measured in the non-linear zone comprises, or consists essentially in, or is, the parameter $\sigma_c$. Preferably, the rheological parameter determined or measured in the zone comprises, or consists essentially in, or is, G*. Indeed, the Inventors have shown that the diagnosis, the stratification, the prognosis and/or the monitoring of a lung disease and/or a respiratory disease is(are) particularly precise and determining when the parameter determined or measured in the non-linear zone is the parameter $\sigma_c$. In the same way, the Inventors have shown that the diagnosis, the stratification, the prognosis and/or the monitoring of a lung disease and/or a respiratory disease is(are) particularly precise and determining when the parameter determined or measured in the linear zone is the parameter G*.

Advantageously, the in vitro method for diagnosing, stratifying, prognosing and/or monitoring a lung disease and/or a respiratory disease, comprises at least the determination or the measurement of the value $A_{nl}$ of a rheological parameter in a non-linear zone of the deformation curve of the sample.

Preferably, the in vitro method for diagnosing, stratifying, prognosing and/or monitoring a lung disease and/or a respiratory disease, comprises at least the determination or the measurement of the value $A_{nl}$ of a rheological parameter in a non-linear zone of the deformation curve of the sample and at least the determination or the measurement of the value $A_l$ of a rheological parameter in a linear zone of the deformation curve of the sample, said parameters being such as defined above. Indeed, the Inventors have shown that the diagnosis, the stratification, the prognosis and/or the monitoring of a lung disease and/or a respiratory disease is(are) particularly precise and determining when both a rheological parameter in the non-linear zone and a rheological parameter in the non-linear zone of the deformation curve are determined.

Thus, according to a particularly preferred embodiment, the present invention relates to an in vitro method for diagnosing, stratifying, prognosing and/or monitoring a lung disease and/or a respiratory disease, comprising:
  (i) the determination or the measurement of the value $A_{nl}$ of at least one rheological parameter on a sample of mucus A of a subject, in a non-linear zone of the deformation curve of the sample; and
  (ii) the determination or the measurement of the value $A_l$ of at least one rheological parameter on said sample of mucus A, in a linear zone of the deformation curve of the sample;

wherein the rheological parameter is chosen from: the elasticity modulus (G'), the viscosity modulus (G"), the damping factor (tan δ), the complex modulus (G*), the plastic deformation ($\gamma_p$), the critical deformation ($\gamma_c$), the plastic stress ($\tau_p$), the flow stress threshold ($\tau_c$), the elastic force (EF), the critical stress ($\sigma_c$), and any combination thereof;

the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof;

the rheological parameter determined or measured in the non-linear zone comprising at least $\sigma_c$;

the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof;

the rheological parameter determined or measured in the linear zone comprising at least G*.

Advantageously, the method according to the invention is an in vitro method for diagnosing and stratifying, or diagnosing and prognosing, or diagnosing and monitoring, or instead stratifying and prognosing, or stratifying and monitoring, or instead prognosing and monitoring, or instead diagnosing and stratifying and prognosing, or diagnosing and stratifying and monitoring, or diagnosing and prognosing and monitoring, or instead stratifying and prognosing and monitoring, or instead diagnosing and stratifying and prognosing and monitoring, a lung disease and/or a respiratory disease.

The present invention further relates to an in vitro method for evaluating the effectiveness of a treatment of a lung disease and/or a respiratory disease, comprising:
  (i) the determination or the measurement of the value $A_{nl}$ of at least one rheological parameter on a sample of mucus A of a subject suffering from the lung disease and/or the respiratory disease and having received at least one administration of said treatment, in a non-linear zone of the deformation curve of the sample; and/or
  (ii) the determination or the measurement of the value $A_l$ of at least one rheological parameter on said sample of mucus A, in a linear zone of the deformation curve of the sample;
wherein the linear rheological parameter is chosen from:
  the elasticity modulus (G'),
  the viscosity modulus (G"),
  the damping factor (tan δ),
  the complex modulus (G*),
  the plastic deformation ($\gamma_p$),
  the critical deformation ($\gamma_c$),
  the plastic stress ($\tau_p$),
  the flow stress threshold ($\tau_c$),
  the elastic force (EF),
  the critical stress ($\sigma_c$), and
  any combination thereof;
the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof; further preferably, the determination of the value $A_{nl}$ comprises at least the determination of the value of the rheological parameter $\sigma_c$;

the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof; further preferably, the determination of the value $A_l$ comprises at least the determination of the value of the rheological parameter G*.

Preferably, the in vitro method for evaluating the effectiveness of a treatment of a lung disease and/or a respiratory disease, comprises at least the determination or the measurement of a rheological parameter chosen from $\sigma_c^*$. Advantageously, the determination or the measurement of the value $A_{nl}$ of at least one rheological parameter on a sample of mucus A of a subject, in a non-linear zone of the deformation curve of the sample, comprises at least the determination or the measurement of the value $A_{nl}$ of the rheological parameter $\sigma_c$. Alternatively or in combination, the determination or the measurement of the value $A_l$ of at least one rheological parameter on a sample of mucus A of a subject, in a linear zone of the deformation curve of the sample, comprises at least the determination or the measurement of the value $A_l$ of the rheological parameter G*. Preferably, the rheological parameter determined or measured in the non-linear zone comprises, or consists essentially in, or is, the parameter σc. Preferably, the rheological parameter determined or measured in the zone comprises, or consists essentially in, or is, G*. Indeed, the Inventors have shown that the evaluation of the effectiveness of a treatment of a lung disease and/or a respiratory disease is particularly precise and determining when the parameter determined or measured in the non-linear zone is the parameter $\sigma_c$. In the same way, the Inventors have shown that the evaluation of the effectiveness of a treatment of a lung disease and/or a respiratory disease is particularly precise and determining when the parameter determined or measured in the linear zone is the parameter G*.

Advantageously, the in vitro method for evaluating the effectiveness of a treatment of a lung disease and/or a respiratory disease, comprises at least the determination or the measurement of the value $A_{nl}$ of a rheological parameter in a non-linear zone of the deformation curve of the sample.

Preferably, the in vitro method for evaluating the effectiveness of a treatment of a lung disease and/or a respiratory disease, comprises at least the determination or the measurement of the value $A_{nl}$ of a rheological parameter in a non-linear zone of the deformation curve of the sample and at least the determination or the measurement of the value $A_l$ of a rheological parameter in a linear zone of the deformation curve of the sample, said parameters being such as defined above. Indeed, the Inventors have shown that the evaluation of the effectiveness of a treatment of a lung disease and/or a respiratory disease is particularly precise and determining when both a rheological parameter in the non-linear zone and a rheological parameter in the linear zone of the deformation curve are determined.

Thus, according to a particularly preferred embodiment, the present invention relates to an in vitro method for evaluating the effectiveness of a treatment of a lung disease and/or a respiratory disease, comprising:
  (i) the determination or the measurement of the value $A_{nl}$ of at least one rheological parameter on a sample of mucus A of a subject, in a non-linear zone of the deformation curve of the sample; and (ii) the determination or the measurement of the value $A_l$ of at least one rheological parameter on said sample of mucus A, in a linear zone of the deformation curve of the sample;

wherein the rheological parameter is chosen from: the elasticity modulus (G'), the viscosity modulus (G"), the damping factor (tan δ), the complex modulus (G*), the plastic deformation ($\gamma_p$), the critical deformation ($\gamma_c$), the plastic stress ($\tau_p$), the flow stress threshold ($\tau_c$), the elastic force (EF), the critical stress ($\sigma_c$), and any combination thereof;

the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof; the rheological parameter determined or measured in the non-linear zone comprising at least $\sigma_c$, the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof;

the rheological parameter determined or measured in the linear zone comprising at least G*.

The sample of mucus may have been taken by a spontaneous expectoration of a subject. The sample of mucus may also have been obtained by sampling according to different techniques, including for example bronchioalveolar lavage (BAL), throat swab and induced expectoration.

Bronchioalveolar lavage is a technique for sampling during bronchoscopy. The fibroscope is blocked in a peripheral bronchus and physiological serum is injected then sucked back. Precautions must be taken to avoid contamination of the sample taking by nasopharyngeal secretions. A throat swab consists in collecting secretions on a swab, either by scraping the posterior wall of the pharynx or in asking the patient to cough into the swab. Pharyngeal aspiration consists in aspiring the contents of the posterior pharynx using a small catheter, either orally using a tongue depressor, or by nasal route. Induced expectoration consists in favouring expectoration through the inhalation of hypertonic saline (comprising NaCl or other), which makes it possible to increase the volume of secretions and improve mucociliary clearance of the lower airways in subjects who do not spit. Expectoration may notably be induced by inhalation of increasing concentrations (3% to 5%) of hypertonic saline by periods of 5 to 7 minutes, for example using an ultrasonic nebuliser.

The subject may be a healthy subject. The subject may also be a subject liable to have a pulmonary and/or respiratory disease. This may be for example the case when the subject presents symptoms of such a disease, or in the case of predisposition to such a disease. The predisposition may be genetic and/or hereditary. When the invention relates to an in vitro method for diagnosing a lung disease and/or a respiratory disease, the subject is preferably a subject liable to have a pulmonary and/or respiratory disease.

Alternatively, the subject may be a subject suffering from a pulmonary and/or respiratory disease, that is to say a subject in whom said disease is declared and has been diagnosed beforehand. When the invention relates to an in vitro method for stratifying, prognosing and/or monitoring a lung disease and/or a respiratory disease, the subject is preferably a subject suffering from such a disease.

The subject may be under treatment for a pulmonary and/or respiratory disease. This is notably the case when the invention relates to an in vitro method for evaluating the effectiveness of a treatment of a lung disease and/or a respiratory disease. This may be also the case when the invention relates to an in vitro method for diagnosing, stratifying, prognosing and/or monitoring a lung disease and/or a respiratory disease. The treatment may be preventive, for example in the case of predisposition to a disease, or it may be curative, for example in the case of a diagnosed/declared disease. In this case, the subject has received at least one administration of said treatment. The treatment may be a treatment known to those skilled in the art, administered according to a protocol conventionally followed by those skilled in the art for treating the pulmonary and/or respiratory disease from which the patient suffers. They comprise notably bronchodilators, corticosteroids, antibiotics, oxygen therapy, vaccines, monoclonal antibodies (such as Dupilumab), CFTR (cystic fibrosis transmembrane conductance) correctors; treatments targeting the protein CFTR, epithelial sodium channel correctors (ENaC, for Epithelial Na channel), and combinations thereof.

The treatment may also be experimental, that is to say a treatment of which the effects on the respiratory and/or pulmonary disease considered are not yet known (or poorly known). In this case, the methods according to the invention make it possible to evaluate if this treatment may be used to treat the targeted disease. When the invention relates to an in vitro method for stratifying, prognosing and/or monitoring a lung disease and/or a respiratory disease, the treated subject is preferably a subject suffering from such a disease. Those skilled in the art will know how to define the suitable medicine(s) and/or the suitable therapy or therapies to administer to the subject and/or to experiment, as well as the protocol to implement and the modalities of administration, according to the subject considered, the disease diagnosed or suspected and/or the diagnosed or suspected stage of the disease.

Alternatively, the subject may not be under any treatment for a pulmonary and/or respiratory disease. For example, the subject may not have received any administration of a given treatment, known to those skilled in the art for a pulmonary and/or respiratory disease, in the course of a determined period preceding the implementation of a method according to the invention, said period having a duration that can last from one to several weeks (for example 2 to 8 weeks) or instead from one to several months (for example 3 to 10 months) or instead from one to several years (for example 1 to 20 years, or instead 2 to 15 years or instead 3 to 12 years or instead 3 to 10 years). For example, the subject may not have received any administration of a given treatment, known to those skilled in the art for a pulmonary and/or respiratory disease during his lifetime. Those skilled in the art will know how to define the duration of the period preceding the implementation of a method according to the invention during which the subject must not have received a given treatment. This duration could for example depend on the pharmacokinetics of the treatment, its clearance or the time for it to be eliminated from the body.

According to a preferred embodiment of the methods of the invention, the subject is a human.

In order to measure and/or determine the rheological parameter, the sample of mucus is subjected to a deformation or to a stress with a view to generating a curve of the type of FIG. 1. Rheometers conventionally operate:

either by applying a deformation and by measuring the stress (FIG. 1), or by applying a stress and measuring the deformation thereof (in practice via a feedback loop).

This deformation is applied by means of a rheometer, in which the sample is placed between two moveable parts, for example in rotation or in oscillation, one with respect to the other. A first part is rotationally driven with respect to the second part so as to apply a shear stress to the sample. A sensor makes it possible to measure the torque applied by the sample to the second part.

In a particularly advantageous manner, the surface of each part in contact with the sample has a sufficient roughness to minimise or even avoid the sliding of the sample along said surface.

Different types of rheometers exist, associated with different geometries of the two parts (coaxial cylinders, cone-plane, plane-plane), but the invention is not limited to one particular type of rheometer.

The results presented in the present text were obtained with a plane-plane type rheometer, the characteristics of which are provided hereafter in the section "Material and methods".

According to a preferred embodiment of the methods of the invention, the value $A_l$ of at least one rheological parameter is determined/measured at a deformation less than or equal to 10%, preferably at a deformation less than or equal to 9%, preferably at a deformation less than or equal to 8%, preferably at a deformation less than or equal to 7%, preferably at a deformation less than or equal to 6%, preferably at a deformation less than or equal to 5%, preferably at a deformation less than or equal to 4%, preferably at a deformation less than or equal to 3%, preferably at a deformation less than or equal to 2%, preferably at a deformation less than or equal to 1%. According to a preferred embodiment of the methods of the invention, the value $A_l$ of at least one rheological parameter is determined/measured at a deformation ranging from 0% to 10%, preferably at a deformation ranging from 0.5% to 10%, preferably at a deformation ranging from 1% to 9%, preferably at a deformation ranging from 2% to 8%, preferably at a deformation ranging from 3% to 7%, preferably at a deformation ranging from 4% to 6%, preferably at a deformation of around 5%. According to a preferred embodiment of the methods of the invention, the value $A_l$ of at least one rheological parameter is determined/measured at a deformation of around 10%, preferably of around 9%, preferably of around 8%, preferably of around 7%, preferably of around 6%, preferably of around 5%, preferably of around 4%, preferably of around 3%, preferably of around 2%, preferably of around 1%, preferably of around 0%. According to a preferred embodiment of the methods of the invention, the value $A_l$ of at least one rheological parameter is determined/measured at a deformation equal to 10%, preferably equal to 9%, preferably equal to 8%, preferably equal to 7%, preferably equal to 6%, preferably equal to 5%, preferably equal to 4%, preferably equal to 3%, preferably equal to 2%, preferably equal to 1%, preferably equal to 0%. According to a particularly preferred embodiment, the value $A_l$ of at least one rheological parameter is determined/measured at a deformation equal to 5% or around 5%. According to a particularly preferred embodiment, when the rheological parameter is G', G", G* or tan δ, the value $A_l$ is determined/measured at a deformation equal to 5% or around 5%. Indeed, the clinical data show that different respiratory and/or pulmonary diseases are discriminated in a particularly significant manner when the measurement of the rheological parameters is carried out at a deformation of 5%, notably when the parameter is G', G", G* or tan δ. Further, the data show that the repeatability is particularly good when the measurement of the rheological parameters is carried out at a deformation of 5%.

Alternatively or in combination, the value $A_{nl}$ of at least one rheological parameter is preferably determined/measured at a deformation greater than 10%, preferably at a deformation greater than or equal to 15%, preferably at a deformation greater than or equal to 20%, preferably at a deformation greater than or equal to 30%, preferably at a deformation greater than or equal to 40%, preferably at a deformation greater than or equal to 50%, preferably at a deformation greater than or equal to 60%, preferably at a deformation greater than or equal to 70%, preferably at a deformation greater than or equal to 80%, preferably at a deformation greater than or equal to 90%, preferably at a deformation greater than or equal to 100%, preferably at a deformation greater than or equal to 150%, preferably at a deformation greater than or equal to 200%, preferably at a deformation greater than or equal to 300%, preferably at a deformation greater than or equal to 400%, preferably at a deformation greater than or equal to 500%, preferably at a deformation greater than or equal to 1000%.

The results obtained by the Inventors show that different respiratory and/or pulmonary diseases are discriminated in a particularly precise and significant manner when the measurement of the rheological parameters is carried out at a deformation corresponding to the flow point "c" of the sample of mucus, notably when the parameter is G', G", G*, $\tau_c$, $\sigma_c$, or EF, in particular when the parameter is $\sigma_c$. Further, the data show that the repeatability is particularly good when the measurement of the rheological parameters is carried out at the flow point "c" of the sample of mucus. Thus, according to a preferred embodiment of the methods according to the invention, the value $A_{nl}$ of at least one rheological parameter is determined/measured at the flow point "c" of the sample of mucus. According to a particularly preferred embodiment, when the rheological parameter is G', G", G*, $\tau_c$, $\sigma_c$, or EF, the value $A_{nl}$ is determined/measured "at the flow point "c" of the sample of mucus.

According to an embodiment of the methods according to the invention, the determined/measured value $A_l$ and/or the value $A_{nl}$ is compared with a limit value. This comparison notably makes it possible to determine the diagnosis, the stratification, the prognosis and/or the monitoring of a lung disease and/or a respiratory disease in the subject, and/or to determine the effectiveness of a treatment of a lung disease and/or a respiratory disease in a subject having received at least one administration of said treatment.

According to a particular embodiment of the methods according to the invention, the subject has a lung disease and/or a respiratory disease, or the prognosis of a lung disease and/or a respiratory disease is negative, or a lung disease and/or a respiratory disease is exacerbated, or the treatment of a lung disease and/or a respiratory disease is ineffective or not very effective, if at least one of the determined/measured values $A_l$ and/or $A_{nl}$ is different from the limit value.

According to a preferred embodiment, the subject has a lung disease and/or a respiratory disease, or the prognosis of a lung disease and/or a respiratory disease is negative, or a lung disease and/or a respiratory disease is exacerbated, or the treatment of a lung disease and/or a respiratory disease is ineffective or not very effective, if at least one of the determined/measured values $A_l$ and/or $A_{nl}$ is greater than the limit value, when:
the limit value is the value of a rheological parameter determined/measured on the mucus of a healthy reference subject; or the average of the values of a rheological parameter determined/measured on different samples of mucus from a same healthy reference subject (values determined/measured on samples of mucus taken at separate time intervals on the same reference subject or values determined/measured on the same sample of mucus at separate time intervals); or the average of the values of a rheological parameter determined/measured on the mucus of several healthy reference subjects (at least two healthy reference subjects); or the value of a rheological parameter determined/measured on the mucus of a reference subject at a mild or moderate stage of the lung disease and/or the respiratory disease; or the average of the values of a rheological parameter determined/measured on different samples of mucus from a same reference subject at a mild or moderate stage of the lung disease and/or the respiratory disease (values determined/measured on samples of mucus taken at separate time intervals on the same reference subject or values determined/measured on the same sample of mucus at separate time intervals); or the average of the values of a rheological parameter determined/measured on the mucus of several reference subjects at a mild or moderate stage of the lung disease and/or the respiratory disease (at least two reference subjects at a known stage of the lung disease and/or the respiratory disease); and the rheological parameter determined/measured in the non-linear zone is chosen from, and/or comprises, or consists essentially in, or consists in, at least one from among, G', G", G*, $\gamma_c$, $\tau_c$, $\sigma_c$, EF, and any combination thereof, preferably the rheological parameter determined/measured in the non-linear zone is chosen from, and/or comprises, or consists essentially in, or consists in, at least one from among, G', G", G*, $\sigma_c$, EF, and any combination thereof, further preferably the rheological parameter determined/measured in the non-linear zone is chosen from, and/or comprises, or consists essentially in, or consists in, at least one from among, G*, $\sigma_c$, and EF, further preferably from among EF, $\sigma_c$, and any combination thereof; further preferably, the rheological parameter determined/measured in the non-linear zone comprises at least $\sigma_c$, or consists essentially in $\sigma_c$, or $\sigma_c$; and/or the rheological parameter determined/measured in the linear zone is chosen from, and/or comprises, or consists essentially in, or consists in, at least one from among, G', G", G*, $\gamma_p$, $\tau_p$, and any combination thereof, preferably the rheological parameter measured in the linear zone is chosen from, and/or comprises, or consists essentially in, or consists in, at least one from among, G', G", G*, and any combination thereof; further preferably the rheological parameter determined/measured in the linear zone comprises at least G*, or consists essentially in G*, or is G*.

Conversely, according to a preferred embodiment, the subject does not have a lung disease and/or a respiratory disease, or the prognosis of a lung disease and/or a respiratory disease is positive, or a lung disease and/or a respiratory disease is not exacerbated, or the treatment of a lung disease and/or a respiratory disease is effective if at least one of the determined/measured values $A_l$ and/or $A_{nl}$ is less than the limit value, when:

the limit value is the value of a rheological parameter determined/measured on the mucus of a healthy subject; or the average of the values of a rheological parameter determined/measured on different samples of mucus from a same healthy reference subject (values determined/measured on samples of mucus taken at separate time intervals on the same reference subject or values determined/measured on the same sample of mucus at separate time intervals); or the average of the values of a rheological parameter determined/measured on the mucus of several healthy reference subjects (at least two healthy reference subjects); or to the value of a rheological parameter determined/measured on the mucus of a reference subject at a mild or moderate stage of the lung disease and/or the respiratory disease; or the average of the values of a rheological parameter determined/measured on different samples of mucus from a same reference subject at a mild or moderate stage of the lung disease and/or the respiratory disease (values determined/measured on samples of mucus taken at separate time intervals on the same reference subject or values determined/measured on the same sample of mucus at separate time intervals); or the average of the values of a rheological parameter determined/measured on the mucus of several reference subjects at a mild or moderate stage of the lung disease and/or the respiratory disease (at least two reference subjects at a known stage of the lung disease and/or the respiratory disease); and the rheological parameter determined/measured in the non-linear zone is chosen from, and/or comprises, or consists essentially in, or consists in, at least one from among, G', G", G*, $\gamma_c$, $\tau_c$, $\sigma_c$, EF, and any combination thereof, preferably the rheological parameter determined/measured in the non-linear zone is chosen from, and/or comprises, or consists essentially in, or consists in, at least one from among, G', G", G*, $\sigma_c$, EF, and any combination thereof, further preferably the rheological parameter determined/measured in the non-linear zone is chosen from, and/or comprises, or consists essentially in, or consists in, at least one from among, G*, $\sigma_c$, and EF, further preferably from among EF, $\sigma_c$, and any combination thereof; further preferably, the rheological parameter determined/measured in the non-linear zone comprises at least $\sigma_c$, or consists essentially in $\sigma_c$, or $\sigma_c$; and/or the rheological parameter determined/measured in the linear zone is chosen from, and/or comprises, or consists essentially in, or consists in, at least one from among, G', G", G*, $\gamma_p$, $\tau_p$, and any combination thereof, preferably the rheological parameter measured in the linear zone is chosen from, and/or comprises, or consists essentially in, or consists in, at least one from among, G', G", G*, and any combination thereof; further preferably the rheological parameter determined/measured in the linear zone comprises at least G*, or consists essentially in G*, or is G*.

According to a preferred embodiment, the subject has a lung disease and/or a respiratory disease, or the prognosis of a lung disease and/or a respiratory disease is negative, or a lung disease and/or a respiratory disease is exacerbated, or the treatment of a lung disease and/or a respiratory disease is ineffective or not very effective, if at least one of the determined/measured values $A_l$ and/or $A_{nl}$ is less than the limit value, when:

the limit value is the value of a rheological parameter determined/measured on the mucus of a healthy subject; or the average of the values of a rheological parameter determined/measured on different samples of mucus from a same healthy reference subject (values determined/measured on samples of mucus taken at separate time intervals on the same reference subject or values determined/measured on the same sample of mucus at separate time intervals); or the average of the values of a rheological parameter determined/measured on the mucus of several healthy reference subjects (at least two healthy reference subjects); or the value of a rheological parameter determined/measured on the mucus of a reference subject at a mild or moderate stage of the lung disease and/or the respiratory disease; or the average of the values of a rheological parameter determined/measured on different samples of mucus from a same reference subject at a mild or moderate stage of the lung disease and/or the respiratory disease (values determined/measured on samples of mucus taken at separate time intervals on the same reference subject or values determined/measured on the same sample of mucus at separate time intervals); or the average of the values of a rheological parameter determined/measured on the mucus of several reference subjects at a mild or moderate stage of the lung disease and/or the respiratory disease (at least two reference subjects at a known stage of the lung disease and/or the respiratory disease); and the rheological parameter determined/measured in the non-linear zone comprises at least tan δ, or consists essentially in tan δ, or is tan δ; and/or the rheological parameter determined/measured in the linear zone comprises at least tan δ, or consists essentially in tan δ, or is tan δ.

Conversely, according to a preferred embodiment, the subject does not have a lung disease and/or a respiratory disease, or the prognosis of a lung disease and/or a respiratory disease is positive, or a lung disease and/or a respiratory disease is not exacerbated, or the treatment of a lung disease and/or a respiratory disease is effective if at least one of the determined/measured values $A_l$ and/or $A_{nl}$ is greater than the limit value, when:

the limit value is the value of a rheological parameter determined/measured on the mucus of a healthy subject; or the average of the values of a rheological parameter determined/measured on different samples of mucus from a same healthy reference subject (values determined/measured on samples of mucus taken at separate time intervals on the same reference subject or values determined/measured on the same sample of mucus at separate time intervals); or the average of the values of a rheological parameter determined/measured on the mucus of several healthy reference subjects (at least two healthy reference subjects); or the value of a rheological parameter determined/measured on the mucus of a reference subject at a mild or moderate stage of the lung disease and/or the respiratory disease; or the average of the values of a rheological parameter determined/measured on different samples of mucus from a same reference subject at a mild or moderate stage of the lung disease and/or the respiratory disease (values determined/measured on samples of mucus taken at separate time intervals on the same reference subject or values determined/measured on the same sample of mucus at separate time intervals); or the average of the values of a rheological parameter determined/measured on the mucus of several reference subjects at a mild or moderate stage of the lung disease and/or the respiratory disease (at least two reference subjects at a known stage of the lung disease and/or the respiratory disease); and the rheological parameter determined/measured in the non-linear zone comprises at least tan δ, or consists essentially in tan δ, or is tan δ; and/or the rheological parameter determined/measured in the linear zone comprises at least tan δ, or consists essentially in tan δ, or is tan δ.

According to a particularly preferred embodiment, the limit value is the value of a rheological parameter determined/measured on the mucus of a healthy reference subject; or the average of the values of a rheological parameter determined/measured on different samples of mucus from a same healthy reference subject (values determined/measured on samples of mucus taken at separate time intervals on the same reference subject (i.e. single subject) or values determined/measured on the same sample of mucus at separate time intervals); or the average of the values of a rheological parameter determined/measured on the mucus of several healthy reference subjects (at least two healthy reference subjects). Preferably, the healthy reference subject does not suffer from any lung and/or respiratory disease.

According to an embodiment, when the limit value of a rheological parameter is chosen from among the value of a rheological parameter determined/measured on the mucus of a reference subject at a known stage of the lung disease and/or the respiratory disease; or the average of the values of a rheological parameter determined/measured on different samples of mucus from a reference subject at a known stage of the lung disease and/or the respiratory disease (values determined/measured on samples of mucus taken at separate time intervals on the same reference subject or values determined/measured on the same sample of mucus at separate time intervals) or to the average of the values of a rheological parameter determined/measured on the mucus of several reference subjects at a known stage of the lung disease and/or the respiratory disease (at least two reference subjects at a known stage of the lung disease and/or the respiratory disease), the subject is:

at the same stage of the disease as the reference subject(s) if at least one of the determined/measured values $A_l$ and/or $A_{nl}$ is equal to the limit value of the rheological parameter, or if at least one of the determined/measured values $A_l$ and/or $A_{nl}$ does not differ by more than 100% from the limit value of the rheological parameter, preferably does not differ by more than 90%, preferably does not differ by more than 80%, preferably does not differ by more than 70%, preferably does not differ by more than 60%, preferably does not differ by more than 50%, preferably does not differ by more than 40%, preferably does not differ by more than 30%, preferably does not differ by more than 20%, preferably does not differ by more than 10%, preferably does not differ by more than 9%, preferably does not differ by more than 8%, preferably does not differ by more than 7%, preferably does not differ by more than 6%, preferably does not differ by more than 5%, preferably does not differ by more than 4%, preferably does not differ by more than 3%, preferably does not differ by more than 2%, preferably does not differ by more than 1% from the limit value of the rheological parameter;

at a higher stage (i.e. more serious/advanced) of the disease than the reference subject(s) if at least one of the determined/measured values $A_l$ and/or $A_{nl}$ is greater by at least 100% of the limit value of the rheological parameter, preferably by at least 150%, preferably by at least 200%, preferably by at least 300%, preferably by at least 400%, when:

the rheological parameter determined/measured in the non-linear zone is chosen from, and/or comprises, or consists essentially in, or consists in, at least one from among, G', G", G*, $\gamma_c$, $\tau_c$, $\sigma_c$, EF, and any combination thereof, preferably the rheological parameter determined/measured in the non-linear zone is chosen from, and/or comprises, or consists essentially in, or consists in, at least one from among, G', G", G*, $\sigma_c$, EF, and any combination thereof, further preferably the rheological parameter determined/measured in the non-linear zone is chosen from, and/or comprises, or consists essentially in, or consists in, at least one from among, G*, $\sigma_c$, and EF, further preferably from among EF, $\sigma_c$, and any combination thereof; further preferably, the rheological parameter determined/measured in the non-linear zone comprises at least $\sigma_c$, or consists essentially in $\sigma_c$, or is $\sigma_c$; and/or the rheological parameter determined/measured in the linear zone is chosen from, and/or comprises, or consists essentially in, or consists in, at least one from among, G', G", G*, $\gamma_p$, $\tau_p$, and any combination thereof, preferably the rheological parameter measured in the linear zone is chosen from, and/or comprises, or consists essentially in, or consists in, at least one from among, G', G", G*, and any combination thereof; further preferably the rheological parameter determined/measured in the linear zone comprises at least G*, or consists essentially in G*, or is G*;

at a lower stage (i.e. milder/more moderate) of the disease than the reference subject(s) if at least one of the determined/measured values $A_l$ and/or $A_{nl}$ is less by at least 100% of the limit value of the rheological parameter, preferably by at least 150%, preferably by at least 200%, preferably by at least 300%, preferably by at least 400%, when:

the rheological parameter determined/measured in the non-linear zone is chosen from, and/or comprises, or consists essentially in, or consists in, at least one from among, G', G", G*, $\gamma_c$, $\tau_c$, $\sigma_c$, EF, and any combination thereof, preferably the rheological parameter determined/measured in the non-linear zone is chosen from, and/or comprises, or consists essentially in, or consists in, at least one from among, G', G", G*, $\sigma_c$, EF, and any combination thereof, further preferably the rheological parameter determined/measured in the non-linear zone is chosen from, and/or comprises, or consists essentially in, or consists in, at least one from among, G*, $\sigma_c$, and EF, further preferably from among EF, $\sigma_c$, and any combination thereof; further preferably, the rheological parameter determined/measured in the non-linear zone comprises at least $\sigma_c$, or consists essentially in $\sigma_c$, or is $\sigma_c$; and/or the rheological parameter determined/measured in the linear zone is chosen from, and/or comprises, or consists essentially in, or consists in, at least one from among, G', G", G*, $\gamma_p$, $\tau_p$, and any combination thereof, preferably the rheological parameter measured in the linear zone is chosen from, and/or comprises, or consists essentially in, or consists in, at least one from among, G', G", G*, and any combination thereof; further preferably the rheological parameter determined/measured in the linear zone comprises at least G*, or consists essentially in G*, or is G*;

at a higher stage (i.e. more serious/advanced) of the disease than the reference subject(s) if at least one of the determined/measured values $A_l$ and/or $A_{nl}$ is less by at least 10% of the limit value of the rheological parameter, preferably by at least 15%, preferably by at least 20%, preferably by at least 30%, preferably by at least 40%, preferably by at least 50%, when:

the rheological parameter determined/measured in the non-linear zone comprises at least tan δ, or consists essentially in tan δ, or is tan δ; and/or the rheological parameter determined/measured in the linear zone comprises at least tan δ, or consists essentially in tan δ, or is tan δ.

The limit values (or ranges) may be as indicated in Table 1 below:

according to a particular embodiment of the methods according to the invention, when the limit value is the average of the values of a rheological parameter determined/measured on the mucus of several healthy reference subjects (at least two healthy reference subjects), and/or according to a particular embodiment of the methods according to the invention, when the limit value is the average of the values of a rheological parameter determined/measured on the mucus of several reference subjects with cystic fibrosis (at least two reference subjects), and/or when the limit value is the average of the values of a rheological parameter determined/measured on the mucus of several reference subjects with COPD (at least two reference subjects), and/or according to a particular embodiment of the methods according to the invention, when the limit value is the average of the values of a rheological parameter determined/measured on the mucus of several reference subjects with asthma (at least two reference subjects):

TABLE 1

Average limit value for reference subjects with cystic fibrosis, reference subjects with COPD, reference subjects with asthma, and healthy reference subjects, with the standard deviations, thus defining a range.

| Limit value Rheological parameter | Reference subjects with cystic fibrosis | Reference subjects with COPD | Reference subjects with asthma | Healthy reference subjects |
|---|---|---|---|---|
| G' measured at 5% deformation (Pa) | 1.354 +/− 2.008 | 0.689 +/− 0.885 | 0.150 +/− 0.194 | 0.085 +/− 0.108 |
| G" measured at 5% deformation (Pa) | 0.508 +/− 0.716 | 0.234 +/− 0.175 | 0.067 +/− 0.082 | 0.0475 +/− 0.082 |
| $G'_c = G''_c$ measured at the flow point c (Pa) | 0.230 +/− 0.161 | 0.195 +/− 0.147 | 0.066 +/− 0.055 | 0.044 +/− 0.028 |

TABLE 1-continued

Average limit value for reference subjects with cystic fibrosis, reference subjects with COPD, reference subjects with asthma, and healthy reference subjects, with the standard deviations, thus defining a range.

| Limit value Rheological parameter | Reference subjects with cystic fibrosis | Reference subjects with COPD | Reference subjects with asthma | Healthy reference subjects |
|---|---|---|---|---|
| $G^*$ at 5 % deformation (Pa) | 1.446 (ranging preferably from 1 to 2.5) | 0.728 (ranging preferably from 0.5 to 0.9) | 0.165 (ranging preferably from 0.15 to 0.3) | 0.0975 (ranging preferably from 0.09 to 0.1) |
| $\sigma_c$ measured at the flow point c (Pa) | 9.756 +/− 5.872 | 10.024 +/− 8.586 | 4.138 +/− 4.586 | 1.440 +/− 1.378 |
| $\tau_p$ measured at the upper limit of the linear domain (Pa) | 8.421 +/− 32.154 | 0.057 +/− 0.079 | 0.015 +/− 0.020 | 0.013 +/− 0.023 |
| tan δ in the linear domain | 0.275 +/− 0.072 | 0.303 +/− 0.103 | 0.378 +/− 0.120 | 0.361 +/− 0.110 |
| tan δ at the flow point c | 1 | 1 | 1 | 1 by definition |
| EF (Pa$^2$) | 3940.245 +/− 14000 | 11.510 +/− 21.453 | 1.321 +/− 1.624 | 0.292 +/− 0.488 |

Thus, in an embodiment, when the value of a rheological parameter determined/measured on the mucus of the subject is equal to the limit value or falls within the range indicated for this parameter in table 1 for reference subjects with cystic fibrosis (second column of table 1), this indicates that the subject has cystic fibrosis; or, preferably, when the value of a rheological parameter determined/measured on the mucus of the subject is equal to the limit value or falls within the range indicated for this parameter in table 1 for reference subjects with cystic fibrosis (second column of table 1), the probability that the subject has cystic fibrosis is high.

In an embodiment, when the value of a rheological parameter determined/measured on the mucus of the subject is equal to the indicated limit value or falls within the range indicated for this parameter in table 1 for reference subjects with COPD (third column of table 1), this indicates that the subject has COPD; or, preferably, when the value of a rheological parameter determined/measured on the mucus of the subject is equal to the limit value or falls within the range indicated for this parameter in table 1 for reference subjects with COPD (third column of table 1), the probability that the subject has COPD is high.

In an embodiment, when the value of a rheological parameter determined/measured on the mucus of the subject is equal to the limit value or falls within the range indicated for this parameter in table 1 for reference subjects with asthma (fourth column of table 1), this indicates that the subject has asthma; or, preferably, when the value of a rheological parameter determined/measured on the mucus of the subject is equal to the limit value or falls within the range indicated for this parameter in table 1 for reference subjects with asthma (fourth column of table 1), the probability that the subject has asthma is high.

According to a preferred embodiment of the methods according to the invention, to determine the limit values, the sample of mucus used may have been obtained by spontaneous expectoration of said subject. The sample of mucus used may also have been obtained by sampling according to different techniques, including for example bronchioalveolar lavage (BAL), pharyngeal swab, pharyngeal aspiration and induced expectoration, preferably by induced expectoration.

According to this preferred embodiment, the limit value is the average of the values of a rheological parameter determined/measured on the mucus of several reference subjects (at least two reference subjects), said subjects being either healthy subjects, or subjects with cystic fibrosis, or reference subjects with COPD or COPD at a severe stage, or reference subjects with asthma or asthma at a severe stage, or reference subjects with bronchiectasis (BTS). According to this preferred embodiment, the limit values (or ranges) may be as indicated in table 2, as follows:

TABLE 2

Average limit value for reference subjects with cystic fibrosis, reference subjects with COPD or COPD at a severe stage, reference subjects with asthma or asthma at a severe stage, reference subjects with bronchiectasis (BTS), and healthy reference subjects, with the standard deviations, thus defining a range.

| Reference subjects | Expectoration | G' (Pa) | G" (Pa) | G* (Pa) | tan δ (−) | $\sigma_c$ (Pa) | EF (Pa$^2$) |
|---|---|---|---|---|---|---|---|
| Healthy | Induced | 0.14 | 0.047 | 0.15 | 0.35 | 0.012 | 0.27 |
| min-max | | 0.07-0.28 | 0.010-0.129 | 0.07-0.28 | 0.14-0.52 | 0.005-0.036 | 0.14-0.62 |
| Asthma | Induced | 0.25 | 0.098 | 0.27 | 0.41 | 0.019 | 0.75 |
| min-max | | 0.07-0.59 | 0.043-0.208 | 0.07-0.59 | 0.22-0.63 | 0.007-0.068 | 0.23-2.81 |
| COPD | Induced | 0.43 | 0.14 | 0.45 | 0.34 | 0.097 | 3.61 |
| min-max | | 0.09-1.88 | 0.03-0.44 | 0.09-1.88 | 0.21-0.48 | 0.024-0.327 | 0.87-11.91 |

TABLE 2-continued

Average limit value for reference subjects with cystic fibrosis, reference subjects with COPD or COPD at a severe stage, reference subjects with asthma or asthma at a severe stage, reference subjects with bronchiectasis (BTS), and healthy reference subjects, with the standard deviations, thus defining a range.

| Reference subjects | Expectoration | G' (Pa) | G'' (Pa) | G* (Pa) | tan δ (−) | $\sigma_c$ (Pa) | EF (Pa$^2$) |
|---|---|---|---|---|---|---|---|
| COPD | Spontaneous | 1.15 | 0.33 | 1.2 | 0.31 | 0.31 | 11.77 |
| min-max | | 0.10-5.54 | 0.05-1.12 | 0.10-5.54 | 0.20-0.52 | 0.03-1.08 | 1.05-38.90 |
| Cystic fibrosis | Induced | 0.84 | 0.28 | 0.89 | 0.35 | 0.21 | 6.34 |
| min-max | | 0.21-3.83 | 0.09-0.76 | 0.21-3.83 | 0.23-0.51 | 0.02-0.59 | 1.03-19.33 |
| Cystic fibrosis | Spontaneous | 1.24 | 0.41 | 1.31 | 0.34 | 0.32 | 9.68 |
| min-max | | 0.23-3.41 | 0.12-1.17 | 0.23-3.41 | 0.28-0.53 | 0.04-0.76 | 1.43-26.00 |
| Severe asthma | Spontaneous | 12.62 | 2.64 | 12.89 | 0.24 | 63.08 | 813 |
| Standard deviation | | 10.06 | 1.74 | 10.33 | 0.06 | 62.86 | 649 |
| Severe COPD | Spontaneous | 3.01 | 0.85 | 3.13 | 0.34 | 24.1 | 75.4 |
| Standard deviation | | 1.43 | 0.18 | 1.42 | 0.16 | 11.92 | 16.9 |
| BTS | Spontaneous | 2.8 | 0.87 | 2.93 | 0.32 | 36.19 | 106 |
| Standard deviation | | 1.83 | 0.45 | 1.86 | 0.08 | 21.4 | 39.8 |

Thus, in this embodiment, when the value of a rheological parameter determined/measured on the mucus of the subject is equal to the limit value or falls within the range indicated for this parameter in table 2 for reference subjects with cystic fibrosis, this indicates that the subject has cystic fibrosis; or, preferably, when the value of a rheological parameter determined/measured on the mucus of the subject is equal to the limit value or falls within the range indicated for this parameter in table 2 for reference subjects with cystic fibrosis, the probability that the subject has cystic fibrosis is high.

In this embodiment, when the value of a rheological parameter determined/measured on the mucus of the subject is equal to the indicated limit value or falls within the range indicated for this parameter in table 2 for reference subjects with COPD, this indicates that the subject has COPD; or, preferably, when the value of a rheological parameter determined/measured on the mucus of the subject is equal to the limit value or falls within the range indicated for this parameter in table 2 for reference subjects with COPD, the probability that the subject has COPD is high.

In an embodiment, when the value of a rheological parameter determined/measured on the mucus of the subject is equal to the limit value or falls within the range indicated for this parameter in table 2 for reference subjects with asthma, this indicates that the subject has asthma; or, preferably, when the value of a rheological parameter determined/measured on the mucus of the subject is equal to the limit value or falls within the range indicated for this parameter in table 2 for reference subjects with asthma, the probability that the subject has asthma is high.

According to an embodiment, the methods according to the invention further comprise the determination or the measurement of the value $B_l$ of at least one rheological parameter (such as defined above) on a second sample of mucus (B) of said subject, in a linear zone of the deformation curve of the sample; and/or the determination or the measurement $B_{nl}$ of at least one rheological parameter (such as defined above) on the second sample (B), in a non linear zone of the deformation curve of the sample; said second sample (B) having been obtained/taken after sample (A), preferably said sample (B) having been obtained at least 24 hours after sample (A), further preferably at least 48 hours after sample (A), further preferably at least 72 hours after sample (A), further preferably at least 7 days after sample (A), further preferably at least 10 days after sample (A), further preferably at least 15 days after sample (A), further preferably at least 1 month after sample (A), further preferably at least 2 months after sample (A), further preferably at least 3 months after sample (A), further preferably at least 4 months after sample (A), further preferably at least 5 months after sample (A), further preferably at least 6 months after sample (A), further preferably at least 7 months after sample (A), further preferably at least 8 months after sample (A), further preferably at least 9 months after sample (A), further preferably at least 10 months after sample (A), further preferably at least 11 months after sample (A), further preferably at least 12 months after sample (A). Further preferably said sample (B) was obtained between 7 days and 6 months after sample (A), further preferably said sample (B) having been obtained between 10 days and 5 months after sample (A), further preferably between 15 days and 4 months, further preferably between 21 days and 3 months, further preferably between 30 and 60, further preferably between 40 and 50 days.

According to an embodiment, the method further comprises the determination of the evolution $E_l$ of the value of the rheological parameter determined/measured in the linear zone of the deformation curve and/or the evolution $E_{nl}$ of the value of the rheological parameter determined/measured in the linear zone of the deformation curve. Advantageously, the evolution $E_l$ of the value of the rheological parameter determined/measured in the linear zone of the deformation curve is determined by comparing the value $B_l$ with the value $A_l$ and/or the evolution $E_{nl}$ of the value of the rheological parameter determined/measured in the linear zone of the deformation curve is determined by comparing the value $B_{nl}$ with the value $A_{nl}$.

In this case, the subject has a lung disease and/or a respiratory disease, or the prognosis of a lung disease and/or a respiratory disease is negative, or a lung disease and/or a respiratory disease is exacerbated, or the treatment of a lung disease and/or a respiratory disease is ineffective or not very effective, if the determined/measured value $B_l$ is different from the determined/measured value $A_l$ for at least one rheological parameter and/or if the determined/measured value $B_{nl}$ is different from the determined/measured value $A_{nl}$ for at least one rheological parameter.

In particular, the subject has a lung disease and/or a respiratory disease, or the prognosis of a lung disease and/or a respiratory disease is negative, or a lung disease and/or a respiratory disease is exacerbated, or the treatment of a lung disease and/or a respiratory disease is ineffective or not very effective, if at least one of the determined/measured values $A_l$ is greater than the value $B_l$ determined/measured for the same rheological parameter, and/or if at least one of the determined/measured values $A_{nl}$ is greater than the value $B_{nl}$ determined/measured for the same rheological parameter, when:

the rheological parameter determined/measured in the non-linear zone is chosen from, and/or comprises, or consists essentially in, or consists in, at least one from among, G', G", G*, $\gamma_c$, $\tau_c$, $\sigma_c$, EF, and any combination thereof, preferably the rheological parameter determined/measured in the non-linear zone is chosen from, and/or comprises, or consists essentially in, or consists in, at least one from among, G', G", G*, $\sigma_c$, EF, and any combination thereof, further preferably the rheological parameter determined/measured in the non-linear zone is chosen from, and/or comprises, or consists essentially in, or consists in, at least one from among, G*, $\sigma_c$, and EF, further preferably from among EF, $\sigma_c$, and any combination thereof; further preferably, the rheological parameter determined/measured in the non-linear zone comprises at least $\sigma_c$, or consists essentially in $\sigma_c$, or is $\sigma_c$; and/or the rheological parameter determined/measured in the linear zone is chosen from, and/or comprises, or consists essentially in, or consists in, at least one from among, G', G", G*, $\gamma_p$, $\tau_p$, and any combination thereof, preferably the rheological parameter measured in the linear zone is chosen from, and/or comprises, or consists essentially in, or consists in, at least one from among, G', G", G*, and any combination thereof; further preferably the rheological parameter determined/measured in the linear zone comprises at least G*, or consists essentially in G*, or is G*.

Conversely, according to a preferred embodiment, the subject does not have a lung disease and/or a respiratory disease, or the prognosis of a lung disease and/or a respiratory disease is positive, or a lung disease and/or a respiratory disease is not exacerbated, or the treatment of a lung disease and/or a respiratory disease is effective, if at least one of the determined/measured values $A_l$ is less than the value $B_1$ determined/measured for the same rheological parameter, and/or if at least one of the determined/measured values $A_{nl}$ is less than the value $B_{nl}$ determined/measured for the same rheological parameter, when:

the rheological parameter determined/measured in the non-linear zone is chosen from, and/or comprises, or consists essentially in, or consists in, at least one from among, G', G", G*, $\gamma_c$, $\tau_c$, $\sigma_c$, EF, and any combination thereof, preferably the rheological parameter determined/measured in the non-linear zone is chosen from, and/or comprises, or consists essentially in, or consists in, at least one from among, G', G", G*, $\sigma_c$, EF, and any combination thereof, further preferably the rheological parameter determined/measured in the non-linear zone is chosen from, and/or comprises, or consists essentially in, or consists in, at least one from among, G*, $\sigma_c$, and EF, further preferably from among EF, $\sigma_c$, and any combination thereof; further preferably, the rheological parameter determined/measured in the non-linear zone comprises at least $\sigma_c$, or consists essentially in $\sigma_c$, or is $\sigma_c$; and/or the rheological parameter determined/measured in the linear zone is chosen from, and/or comprises, or consists essentially in, or consists in, at least one from among, G', G", G*, $\gamma_p$, $\tau_p$, and any combination thereof, preferably the rheological parameter measured in the linear zone is chosen from, and/or comprises, or consists essentially in, or consists in, at least one from among, G', G", G*, and any combination thereof; further preferably the rheological parameter determined/measured in the linear zone comprises at least G*, or consists essentially in G*, or is G*.

According to a preferred embodiment, the subject has a lung disease and/or a respiratory disease, or the prognosis of a lung disease and/or a respiratory disease is negative, or a lung disease and/or a respiratory disease is exacerbated, or the treatment of a lung disease and/or a respiratory disease is ineffective or not very effective, if at least one of the determined/measured values $A_l$ is less than the value $B_l$ determined/measured for the same rheological parameter, and/or if at least one of the determined/measured values $A_{nl}$ is less than the value $B_{nl}$ determined/measured for the same rheological parameter, when:

the rheological parameter determined/measured in the non-linear zone comprises at least tan δ, or consists essentially in tan δ, or is tan δ; and/or the rheological parameter determined/measured in the linear zone comprises at least tan δ, or consists essentially in tan δ, or is tan δ.

Conversely, according to a preferred embodiment, the subject does not have a lung disease and/or a respiratory disease, or the prognosis of a lung disease and/or a respiratory disease is positive, or a lung disease and/or a respiratory disease is not exacerbated, or the treatment of a lung disease and/or a respiratory disease is effective, if at least one of the determined/measured values $A_l$ is greater than the value $B_l$ determined/measured for the same rheological parameter, and/or if at least one of the determined/measured values $A_{nl}$ is greater than the value $B_{nl}$ determined/measured for the same rheological parameter, when:

the rheological parameter determined/measured in the non-linear zone comprises at least tan δ, or consists essentially in tan δ, or is tan δ; and/or the rheological parameter determined/measured in the linear zone comprises at least tan δ, or consists essentially in tan δ, or is tan δ.

According to a particular embodiment, the subject has a lung disease and/or a respiratory disease, or the prognosis of a lung disease and/or a respiratory disease is negative, or a lung disease and/or a respiratory disease is exacerbated, or the treatment of a lung disease and/or a respiratory disease is ineffective or not very effective, if the evolution $E_l$ of the value of the rheological parameter and/or if the evolution $E_{nl}$ of the value of the rheological parameter is different from an evolution threshold (or reference evolution or limit evolution), preferably wherein said evolution threshold is chosen from among: the evolution of the value of a rheological parameter determined/measured on the mucus of a healthy reference subject; or the average of the evolutions of the value of a rheological parameter determined/measured on different samples of mucus from a same healthy reference subject or the average of the evolutions of the value of a rheological parameter determined/measured on the mucus of several healthy reference subjects (at least two healthy reference subjects); or the evolution of the value of a rheological parameter determined/measured on the mucus of a reference subject at a known stage of the lung disease and/or the respiratory disease; or the average of the evolutions of the value of a rheological parameter determined/measured on different samples of mucus from a same reference subject at a known stage of the lung disease and/or the respiratory disease or to the average of the evolutions of the value of a rheological parameter determined/measured on the mucus of several reference subjects at a known stage of the lung disease and/or the respiratory disease (at least two reference subjects at a known stage of the lung disease and/or the respiratory disease).

According to an embodiment of the methods according to the invention, the diagnosis, the prognosis, the stratification and/or the monitoring of the lung disease and/or the respiratory disease further comprise the evaluation of the effectiveness of a treatment of the lung disease and/or the respiratory disease administered to said subject. The effectiveness of a treatment of the lung disease and/or the respiratory disease may be evaluated by using methods known to those skilled in the art. According to an advantageous embodiment, the effectiveness of a treatment of the lung disease and/or the respiratory disease is evaluated by the in vitro method for evaluating the effectiveness of a treatment of a lung disease and/or a respiratory disease according to the present invention (such as defined above). According to this embodiment, the evaluation of the effectiveness of the treatment is preferably based on the value $A_{nl}$, the value $A_l$, the value $B_{nl}$, and/or the value $B_l$, and/or instead on the evolution $E_{nl}$ and or the evolution $E_l$. The evaluation of the effectiveness of a treatment of the lung disease and/or the respiratory disease administered to a subject is notably carried out as described above.

Advantageously, the methods according to the invention further comprise a step (iii) of administration of a treatment to the subject. Those skilled in the art will know how to define the suitable treatment, notably the suitable medicine(s), and/or the suitable therapy or therapies to administer to the subject and/or to experiment, as well as the protocol to implement and the modalities of the administration, according to the considered subject, as well as the diagnosis, stratification, prognosis and/or monitoring resulting from the implementation of a method according to the invention (notably according to the respiratory and/or pulmonary disease diagnosed and/or stratified and/or prognosed and/or monitored Advantageously, the treatment is such as defined above.

Advantageously, the lung disease and/or the respiratory disease is chosen from among COPD, cystic fibrosis and asthma.

The data obtained by the Inventors show that the prior treatment of patients with rhDNase (recombinant human deoxyribonuclease) has an effect on the rheological parameters of the mucus of the patient, thus revealing for the first time that the determination or the measurement of linear and non-linear rheological parameters make it possible to evaluate the mucolytic effect of a treatment. Thus, in an embodiment of the methods according to the present invention, the subject is treated beforehand with rhDNase, before the sample of mucus is taken. Advantageously, the rhDNAse is administered by nebulisation. The modalities of administration of rhDNAse are known to those skilled in the art (notably the doses, the duration of the administration and the type of rhDNAse), in particular according to the considered subject and the respiratory and/or pulmonary disease which the subject has or is liable to have.

The data obtained by the Inventors are all the more relevant when they have been obtained using a device developed by the Inventors, making it possible to simulate the flow of the mucus in physiological situation. The Inventors have notably shown that, thanks to the roughness of the flat surfaces in contact with the sample, this device makes it possible to obtain in a reproducible manner measurements of the viscoelastic and rheological properties of the mucus placed in physiological conditions. Thus, according to an embodiment of the methods according to the invention, the value (Ad), the value (Ai), the value ($B_{nl}$), and/or the value ($B_l$), are measured using a rheological measurement apparatus in which each sample is preferably placed between two slides rotationally moveable with respect to each other, the opposite surfaces of said slides preferably being rough.

Uses of Rheological Parameters as Biomarkers of Respiratory Diseases

The Inventors have thus shown that the rheological parameters measured on a sample of mucus of a subject, as described above, may be used as biomarkers of a respiratory and/or pulmonary disease.

The present invention thus also relates to the use, preferably in vitro, of at least one rheological parameter of a sample of mucus A of a subject, determined or measured in a non-linear zone of the deformation curve of the sample; and/or at least one rheological parameter of said sample of mucus A, determined or measured in a linear zone of the deformation curve of the sample; for diagnosing, stratifying, prognosing and/or monitoring a lung disease and/or a respiratory disease; wherein the rheological parameter is chosen from the elasticity modulus (G'), the viscosity modulus (G''), the damping factor (Tan δ), the complex modulus (G*), the plastic deformation ($\gamma_p$), the critical deformation ($\gamma_c$), the plastic stress ($\tau_p$), the flow stress threshold ($\tau_c$) and the elastic force (EF);

the rheological parameter determined or measured in the non-linear zone preferably being chosen from G', G'', G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof; further preferably, the rheological parameter determined or measured in the non-linear zone comprises at least $\sigma_c$;

the rheological parameter determined or measured in the linear zone preferably being chosen from G', G'', G*, tan δ, $\gamma_p$, $\tau_p$ and any combination thereof; preferably from among G*, tan δ, $\gamma_p$ and any combination thereof; further preferably from among G*, tan δ and any combination thereof; further preferably, the rheological parameter determined or measured in the linear zone comprises at least G*.

The present invention also relates to the use, preferably in vitro, of the value $A_{nl}$ of at least one rheological parameter determined or measured on a sample of mucus A of a subject, in a non-linear zone of the deformation curve of the sample; and/or the value $A_l$ of at least one rheological parameter determined or measured on said sample of mucus A, in a linear zone of the deformation curve of the sample;

for diagnosing, stratifying, prognosing and/or monitoring a lung disease and/or a respiratory disease; wherein the rheological parameter is chosen from the elasticity modulus (G'), the viscosity modulus (G"), the damping factor (Tan δ), the complex modulus (G*), the plastic deformation ($\gamma_p$), the critical deformation ($\gamma_c$), the plastic stress ($\tau_p$), the flow stress threshold ($\tau_c$), the elastic force (EF), the critical stress ($\sigma_c$), and any combination thereof;

the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof; further preferably, the rheological parameter determined or measured in the non-linear zone comprises at least $\sigma_c$;

the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof; further preferably, the rheological parameter determined or measured in the linear zone comprises at least G*.

The Inventors have thus shown that the rheological parameters measured on a sample of mucus of a subject, as described above, may be used as biomarkers for evaluating the effectiveness of a treatment of a respiratory and/or pulmonary disease.

The present invention thus also relates to the use, preferably in vitro, of at least one rheological parameter of a sample of mucus A of a subject suffering from a lung disease and/or a respiratory disease and having received at least one administration of a treatment, determined or measured in a non-linear zone of the deformation curve of the sample; and/or at least one rheological parameter of said sample of mucus A, determined or measured in a linear zone of the deformation curve of the sample; for evaluating the effectiveness of said treatment of said lung disease and/or said respiratory disease; wherein the rheological parameter is chosen from the elasticity modulus (G'), the viscosity modulus (G"), the damping factor (Tan δ), the complex modulus (G*), the plastic deformation ($\gamma_p$), the critical deformation ($\gamma_c$), the plastic stress ($\tau_p$), the flow stress threshold ($\tau_c$), the elastic force (EF), the critical stress ($\sigma_c$), and any combination thereof;

the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof; further preferably, the rheological parameter determined or measured in the non-linear zone comprises at least $\sigma_c$;

the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof; further preferably, the rheological parameter determined or measured in the linear zone comprises at least G*.

The present invention also relates to the use, preferably in vitro, of the value $A_{nl}$ of at least one rheological parameter determined or measured on a sample of mucus A of a subject suffering from a lung disease and/or a respiratory disease and having received at least one administration of a treatment, in a non-linear zone of the deformation curve of the sample; and/or the value $A_l$ of at least one rheological parameter determined or measured on said sample of mucus A, in a linear zone of the deformation curve of the sample; for evaluating the effectiveness of said treatment of said lung disease and/or said respiratory disease; wherein the rheological parameter is chosen from the elasticity modulus (G'), the viscosity modulus (G"), the damping factor (Tan δ), the complex modulus (G*), the plastic deformation ($\gamma_p$), the critical deformation ($\gamma_c$), the plastic stress ($\tau_p$), the flow stress threshold ($\tau_c$), the elastic force (EF), the critical stress ($\sigma_c$), and any combination thereof;

the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof; further preferably, the rheological parameter determined or measured in the non-linear zone comprises at least $\sigma_c$;

the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof; further preferably, the rheological parameter determined or measured in the linear zone comprises at least G*.

The present invention also relates to the use, preferably in vitro, of the value $A_{nl}$ of at least one rheological parameter determined or measured on a sample of mucus A of a subject, in a non-linear zone of the deformation curve of the sample; and/or the value $A_l$ of at least one rheological parameter determined or measured on said sample of mucus A, in a linear zone of the deformation curve of the sample; as biomarker for diagnosing, stratifying, prognosing and/or monitoring a lung disease and/or a respiratory disease; and/or as biomarker for evaluating the effectiveness of a treatment of a lung disease and/or a respiratory disease (in this case said subject suffers from the lung disease and/or from the respiratory disease and has received at least one administration of said treatment);

wherein the rheological parameter is chosen from the elasticity modulus (G'), the viscosity modulus (G"), the damping factor (Tan δ), the complex modulus (G*), the plastic deformation ($\gamma_r$), the critical deformation ($\gamma_c$), the plastic stress ($\tau_p$), the flow stress threshold ($\tau_c$), the elastic force (EF), the critical stress ($\sigma_c$), and any combination thereof;

the rheological parameter determined or measured in the non-linear zone preferably being chosen from G', G", G*, tan δ, $\gamma_c$, $\tau_c$, EF, $\sigma_c$, and any combination thereof; preferably from among G*, tan δ, $\tau_c$, EF, $\sigma_c$, and any combination thereof; further preferably from among $\tau_c$, EF, $\sigma_c$, and any combination thereof; further preferably from among $\tau_c$, $\sigma_c$, and any combination thereof; further preferably, the rheological parameter determined or measured in the non-linear zone comprises at least $\sigma_c$;

the rheological parameter determined or measured in the linear zone preferably being chosen from G', G", G*, tan δ, $\gamma_p$, $\tau_p$ and any combination thereof; preferably from among G*, tan δ, $\gamma_p$ and any combination thereof; further preferably from among G*, tan δ and any combination thereof; further preferably, the rheological parameter determined or measured in the linear zone comprises at least G*.

Companion Test

The present invention further relates to a companion test, comprising:
(i) the determination or the measurement of the value $A_{nl}$ of at least one rheological parameter on a sample of mucus A of a subject, in a non-linear zone of the deformation curve of the sample; and/or
(ii) the determination or the measurement of the value $A_l$ of at least one rheological parameter on said sample of mucus A, in a linear zone of the deformation curve of the sample;
wherein the rheological parameter is chosen from:
  the elasticity modulus (G'),
  the viscosity modulus (G"),
  the damping factor (tan δ),
  the complex modulus (G*),
  the plastic deformation ($γ_p$),
  the critical deformation ($γ_c$),
  the plastic stress ($τ_p$),
  the flow stress threshold ($τ_c$),
  the elastic force (EF),
  the critical stress ($σ_c$), and
  any combination thereof;
the rheological parameter determined or measured in the non-linear zone preferably being chosen from G', G", G*, tan δ, $γ_c$, $τ_c$, EF, $σ_c$, and any combination thereof; preferably from among G*, tan δ, $τ_c$, EF, $σ_c$, and any combination thereof; further preferably from among $τ_c$, EF, $σ_c$, and any combination thereof; further preferably from among $τ_c$, $σ_c$, and any combination thereof; further preferably, the rheological parameter determined or measured in the non-linear zone comprises at least $σ_c$;
the rheological parameter determined or measured in the linear zone preferably being chosen from G', G", G*, tan δ, $γ_p$, $τ_p$ and any combination thereof; preferably from among G*, tan δ, $γ_p$ and any combination thereof; further preferably from among G*, tan δ and any combination thereof; further preferably, the rheological parameter determined or measured in the linear zone comprises at least G*.

Advantageously, the rheological parameters of the uses according to the invention and/or the companion test according to the invention, as well as their determination/measurement, the subject and the sample of mucus, are such as defined above in connection with the in vitro method for diagnosing, stratifying, prognosing and/or monitoring a lung disease and/or a respiratory disease and/or with the in vitro method for evaluating the effectiveness of a treatment of a lung disease and/or a respiratory disease.

According to an embodiment of the uses and/or the companion test, the determined/measured value $A_l$ and/or the value $A_{nl}$ is compared with a limit value. Advantageously, this limit value is such as defined above in connection with the in vitro method for diagnosing, stratifying, prognosing and/or monitoring a lung disease and/or a respiratory disease and/or with the in vitro method for evaluating the effectiveness of a treatment of a lung disease and/or a respiratory disease. Further, the use of this limit value, its comparison with the determined/measured value A, and/or the value $A_{nl}$, and/or the conclusions that are drawn therefrom with regard to the condition of the patient, are preferably such as defined above in connection with the in vitro method for diagnosing, stratifying, prognosing and/or monitoring a lung disease and/or a respiratory disease and/or with the in vitro method for evaluating the effectiveness of a treatment of a lung disease and/or a respiratory disease.

EXAMPLES

1. Clinical Study No 1: Subjects with Cystic Fibrosis, COPD or Asthma 1.1. Materials and Methods The clinical protocol NCT02682290 was conducted by the CHU Grenoble-Alpes (CHUGA). Four groups of patients were retained: 11 healthy subjects (HV, for "Healthy Volunteers"), 11 with cystic fibrosis (CF), 11 with chronic obstructive pulmonary disease (COPD) and 12 asthmatics (AS or Ast, for "Asthma").

Inclusion criteria: CF patients (with cystic fibrosis), COPD (all classes), asthmatic with bronchial ailment confirmed by the CHUGA. For the healthy volunteers: men or women more than 18 years old, Body Mass Index (BMI) >18 and <29, non-smokers, absence of any acute pathology in the preceding months, person affiliated to the French health insurance scheme or beneficiary of such a scheme.

Exclusion criteria: FEV1≤40%, PaO2<60 mmHg at rest, acute exacerbation during the preceding month, contraindications for spirometry.

Two visits V1 and V2 were made at 48 h interval. The CF and COPD patients expectorate spontaneously, for the HV and Ast expectoration is induced by 4.5% saline solution for 10 min (standard protocol). The saliva is separated and the sample is homogenised according to the protocol described in WO/2019/020932 (Method for Processing a Sputum Sample and Method for the Rheometric Measurement of a Preprocessed Sample of This Kind). The first sample expectorated is separated into two, one for immediate measurement, the other for a repetition at 10 min.

The rheological tests are carried out at 37° C. with the Rheomuco apparatus (Rheonova, France). Rheomuco is a rotating plane-plane rheometer with imposed deformation. The slides in contact with the mucus are roughened (regular arrangement of pyramids with square base, of base 0.5 mm and height 0.25 mm) to guarantee adhesion up to the flow point.

A sequence of oscillations at 1 Hz is applied with an increasing amplitude by steps of 0.1 to 3000% in order to extract the rheological properties of the mucus in the linear (small deformations, typically <20%) and non-linear (large deformations) domains.

The monitoring protocol is identical for V2, except for the CF: the initial spontaneous expectoration is followed by a nebulisation of rhDNase for 20 min, then a new spontaneous expectoration 1 h later.

1.2. Results

The p values are given in comparison with healthy subjects.

Figure 2:
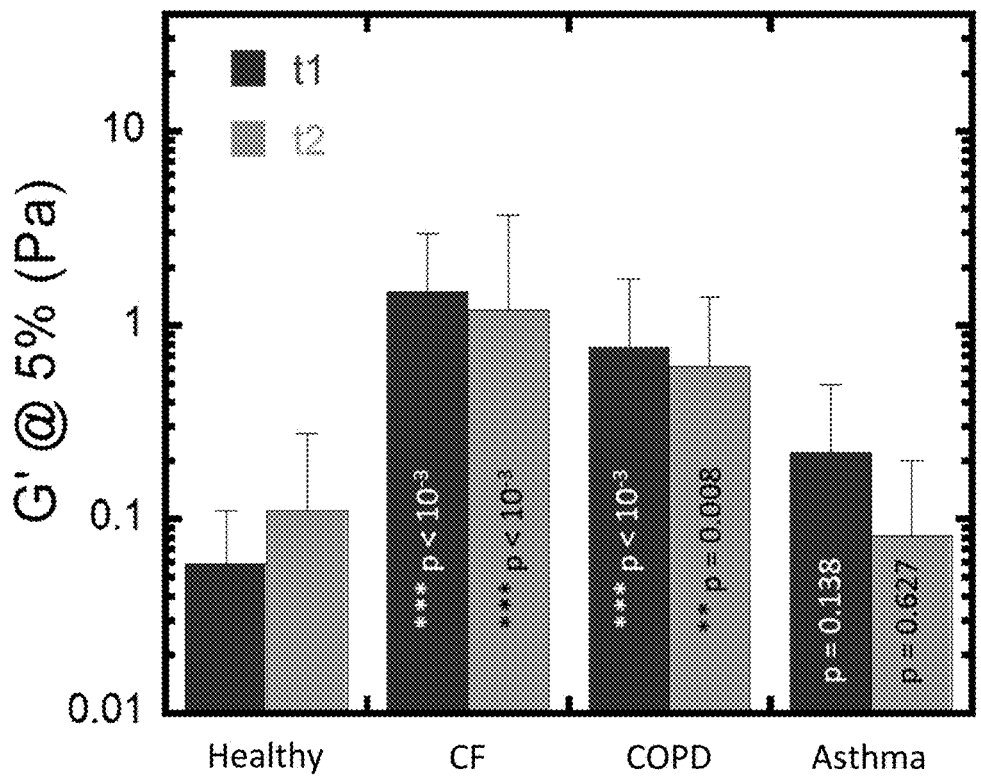
FIG. 2 represents a graph showing the average of the values obtained for the parameter G' measured at 5% deformation, in healthy subjects or patients suffering from cystic fibrosis (CF), COPD or asthma, measured at t1 (black) and t2=t1+10 minutes (grey).
Figure 4:
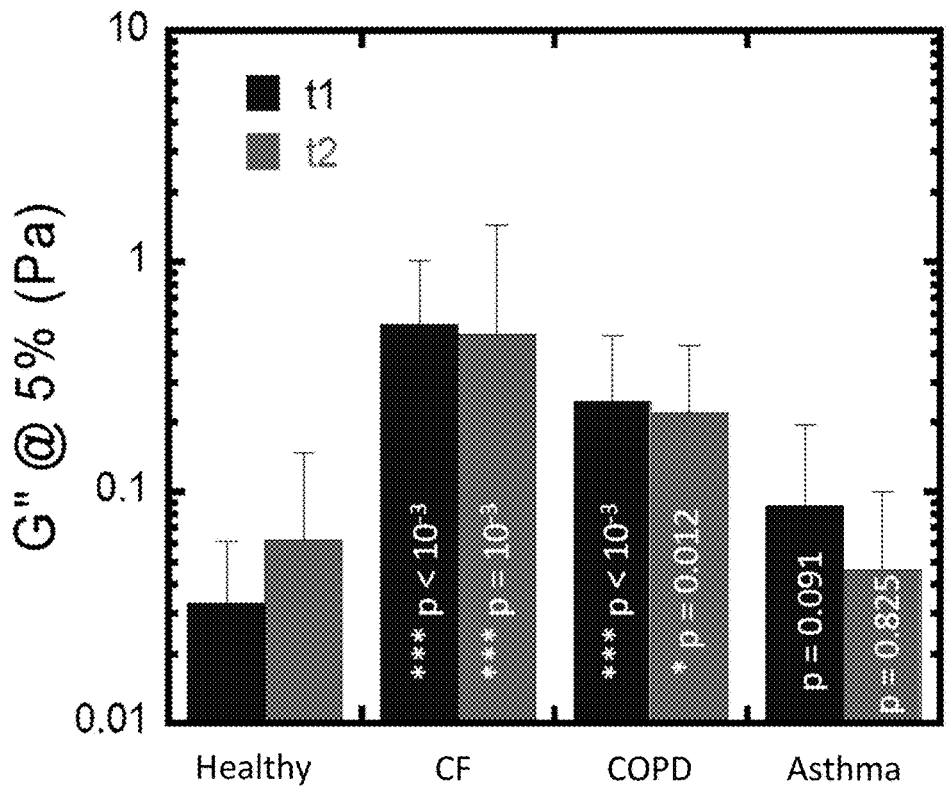
FIG. 4 is a graph showing the average of the values obtained for the parameter G" measured at 5% deformation, in healthy subjects or patients suffering from cystic fibrosis (CF), COPD or asthma, measured at t1 (black) and t2=t1+10 minutes (grey).

The data show that the moduli G', G" and G* measured in the linear zone of the deformation curve (at 5% deformation) are selective markers: the 3 pathologies are clearly discriminated. The repeatability at 10 min is very good (FIGS. 2 and 4 and Tables 3 and 4).

Figure 5:
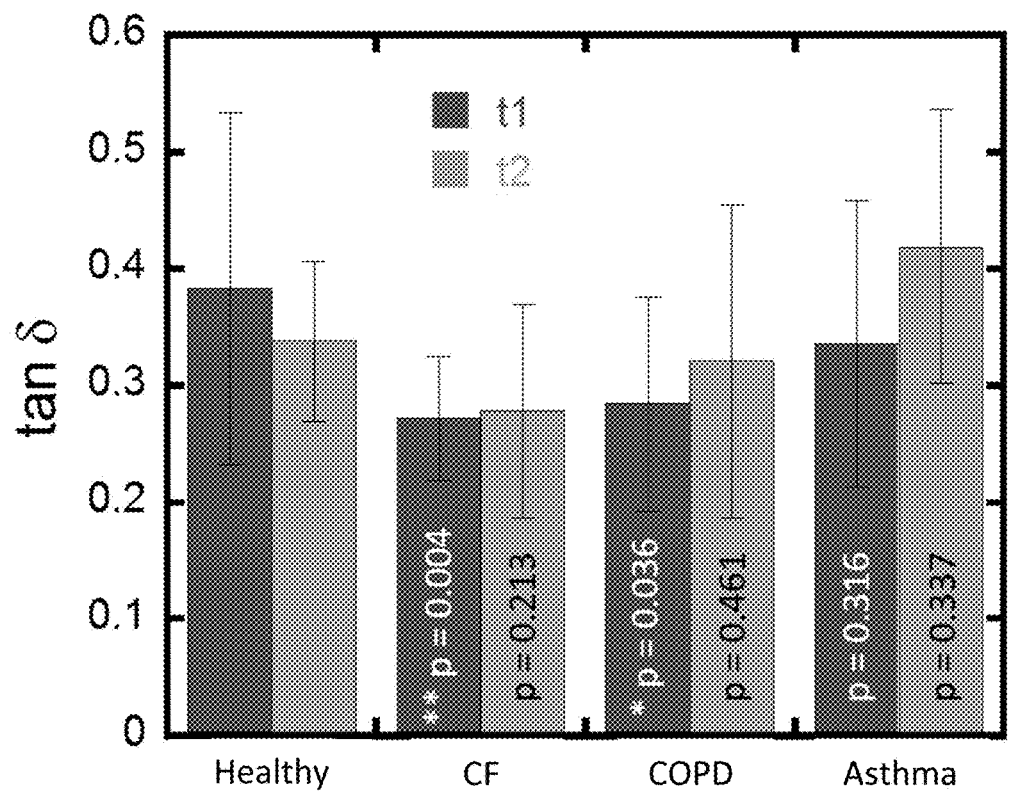
FIG. 5 is a graph showing the average of the values obtained for the parameter tan δ determined in the linear domain, in healthy subjects or in patients suffering from cystic fibrosis (CF), COPD or asthma, determined at t1 (black) and t2=t1+10 minutes (grey).

The marker tan δ (damping factor) shows a slight drop for patients suffering from cystic fibrosis or COPD compared to healthy subjects, statistically significant but not with regard to the variability of the sample. The repeatability at 10 min is good (FIG. 5 and Tables 3 and 4).

Figure 3:
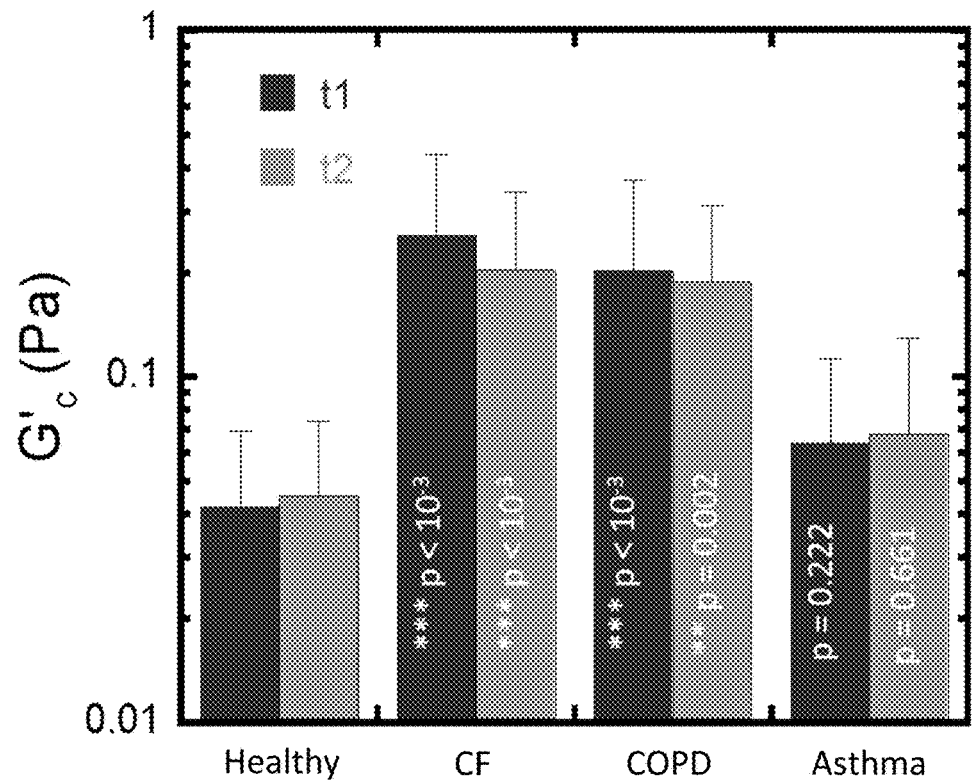
FIG. 3 is a graph showing the average of the values obtained for the parameter G' measured at the flow point c ($G'_c$), in healthy subjects or patients suffering from cystic fibrosis (CF), COPD or asthma, measured at t1 (black) and t2=t1+10 minutes (grey).
Figure 6:
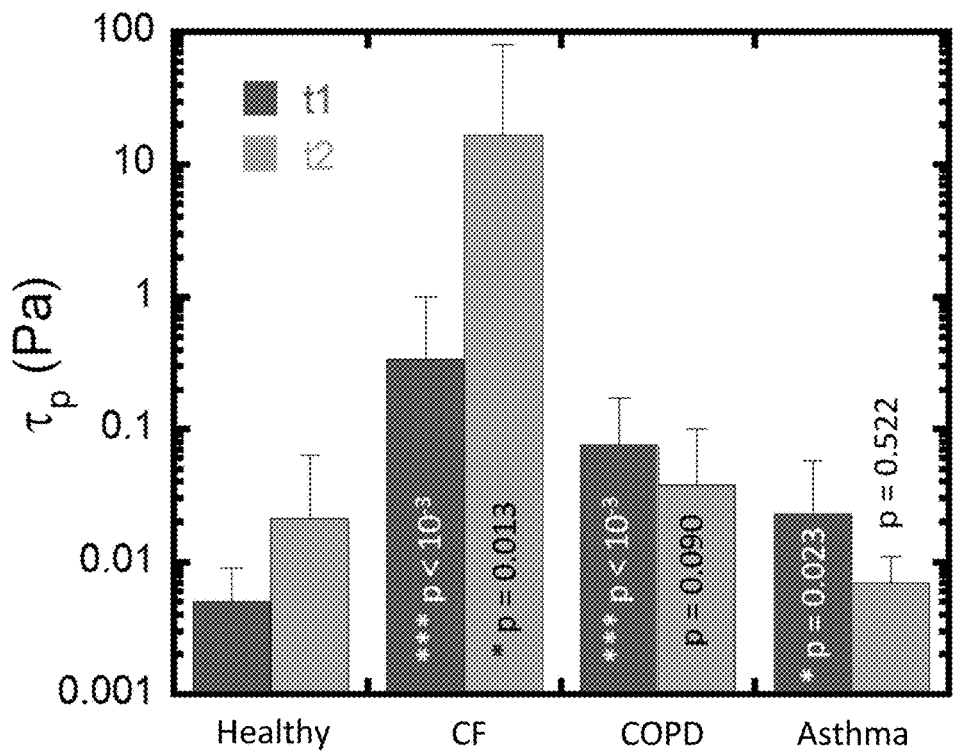
FIG. 6 is a graph showing the average of the values obtained for the parameter τ measured at the upper limit of the linear domain ($τ_p$) (corresponding to the end of plateau zone of the deformation curve), in healthy subjects or in patients suffering from cystic fibrosis (CF), COPD or asthma, measured at t1 (black) and t2=t1+10 minutes (grey).
Figure 7:
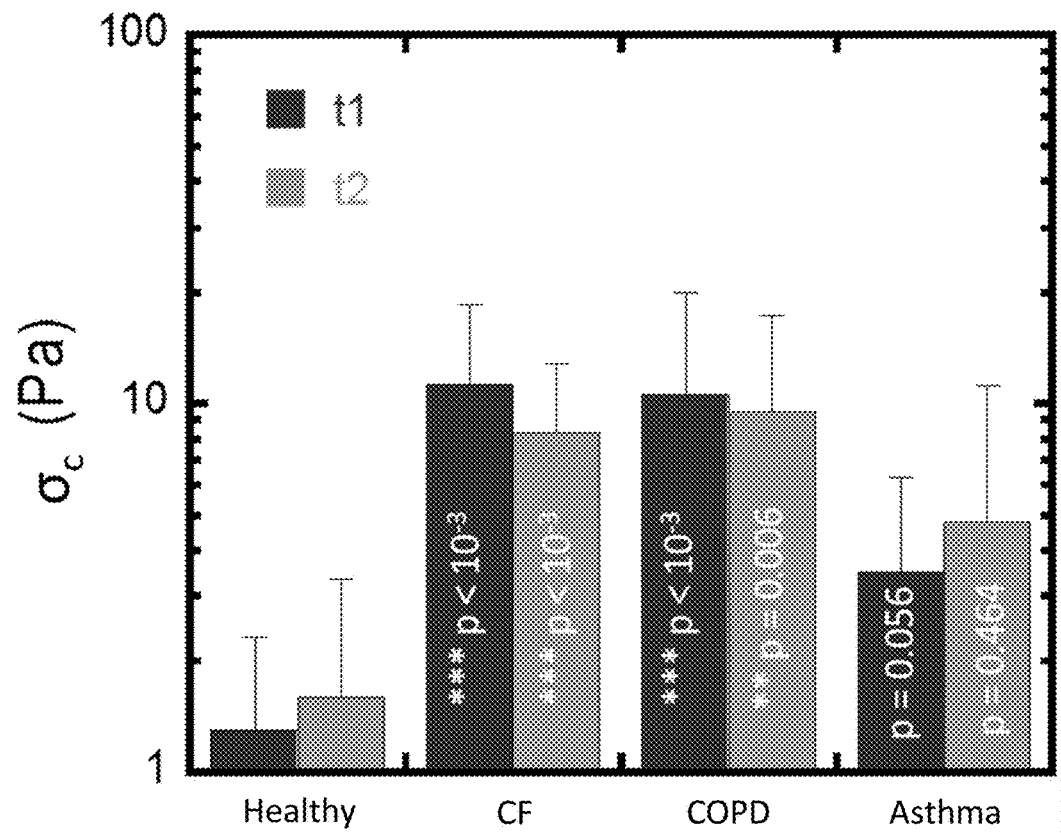
FIG. 7 is a graph showing the average of the values obtained for the parameter σ measured at the flow point c ($σ_c$), in healthy subjects or in patients suffering from cystic fibrosis (CF), COPD or asthma, measured at t1 (black) and t2=t1+10 minutes (grey).

The modulus G', and the stress threshold $τ_c$ (flow stress threshold) measured at the flow point c of the deformation curve distinguish quite clearly healthy and pathological states, despite a slight overlapping of patients with cystic fibrosis or COPD (FIGS. 3 and 7 and Tables 3 and 4). The plastic stress $τ_p$ measured at the upper limit of the linear zone also shows good discrimination of pathologies. However, the repeatability is less good (FIG. 6 and Tables 3 and 4).

Figure 8:
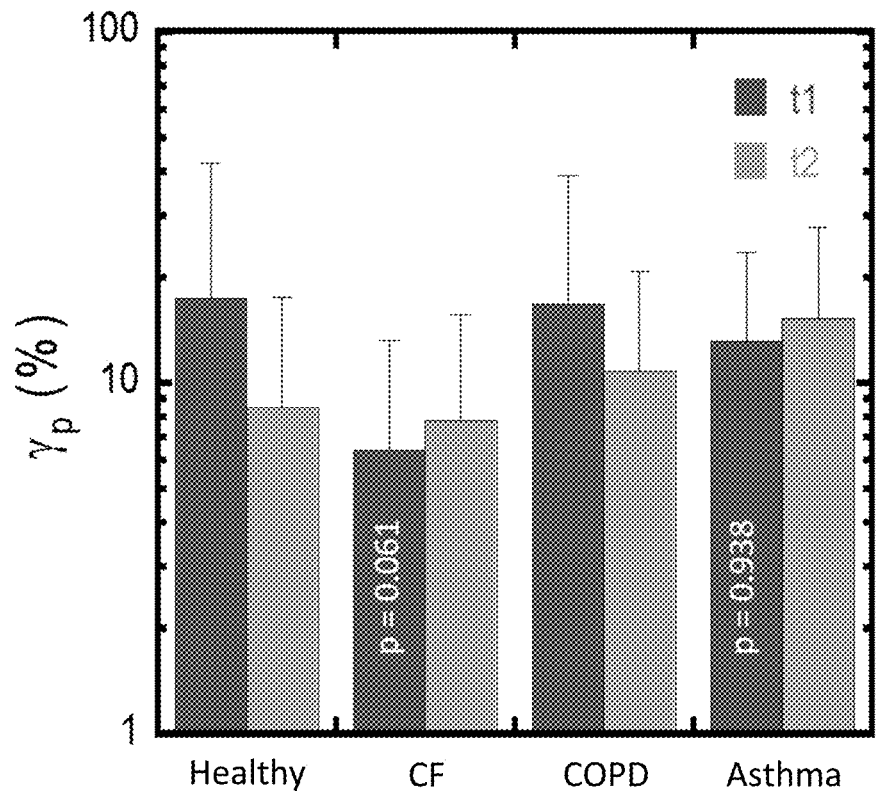
FIG. 8 is a graph showing the average of the values obtained for the parameter γ corresponding to the upper limit of the linear domain ($γ_p$) (corresponding to the end of plateau zone), in healthy subjects or in patients suffering from cystic fibrosis (CF), COPD or asthma, measured at t1 (black) and t2=t1+10 minutes (grey).
Figure 9:
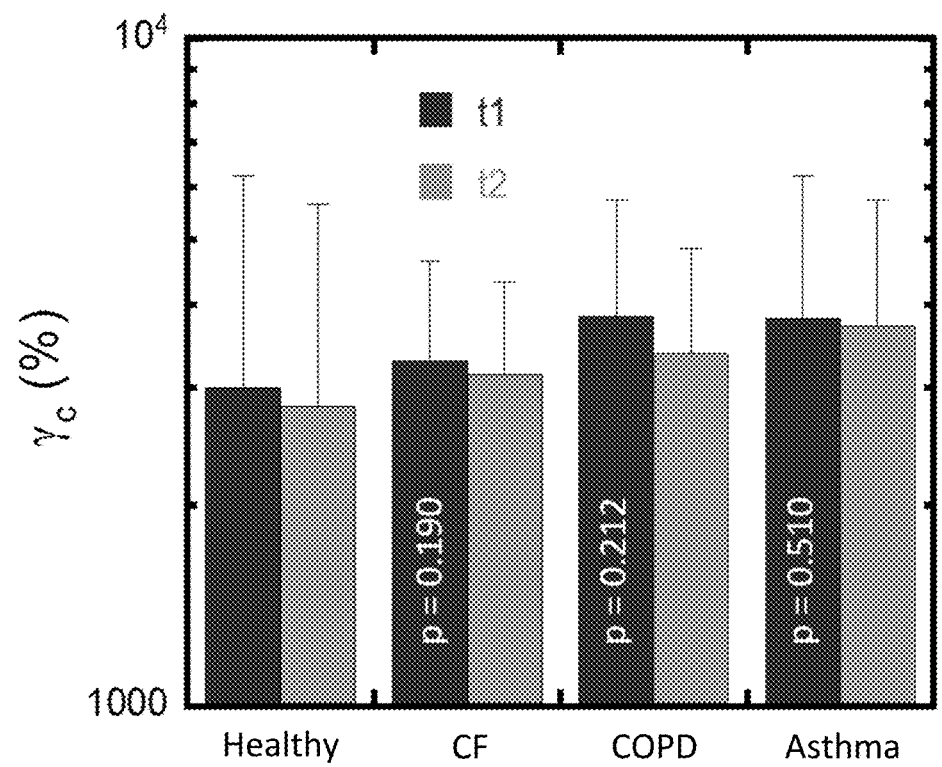
FIG. 9 is a graph showing the average of the values obtained for the parameter γ measured at the flow point c ($γ_c$), in healthy subjects or in patients suffering from cystic fibrosis (CF), COPD or asthma, measured at t1 (black) and t2=t1+10 minutes (grey).

The deformation γ corresponding to transitions between regimes is globally independent of the pathological state, not just at the upper limit of the linear zone ($\gamma_p$) but also at the flow point c ($\gamma_c$). The repeatability at 10 min is very good (FIGS. 8 and 9 and Tables 3 and 4).

EF is defined by the product of the elasticity modulus G* measured in the linear zone (plateau, measured at a deformation of 5%) of the deformation curve by the critical stress $\sigma_c$, measured at the flow point c of the deformation curve. These two parameters being individually discriminating, their product accentuates the differences between populations. On the other hand the variabilities are added together, the average observed on G' for patients with cystic fibrosis leading to a difference between $t_1$ and $t_2$ (FIG. 10 and Tables 3 and 4).

stratification or instead the monitoring of respiratory diseases, but also for the evaluation of the effectiveness of a treatment of these diseases.

Figure 10:
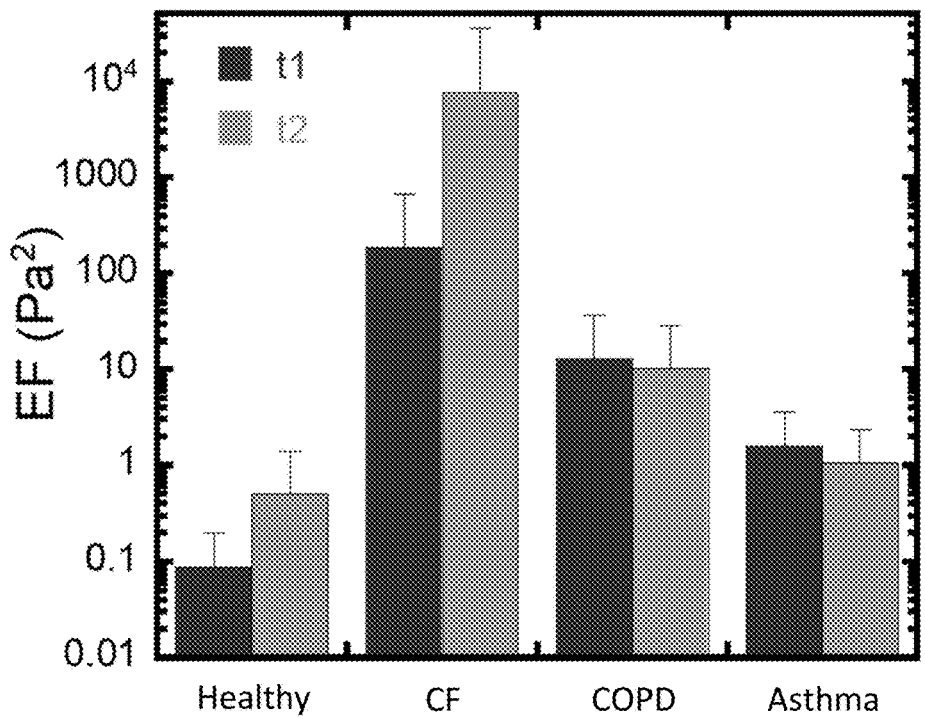
FIG. 10 is a graph showing the average of the values obtained for the parameter EF, determined in healthy subjects or in patients suffering from cystic fibrosis (CF), COPD or asthma, determined at t1 (black) and t2=t1+10 minutes (grey).

The evolution of the biomarkers before/after treatment of patients with cystic fibrosis with rhDNase (n=7 patients) is shown in FIG. 10.

A reduction (non-significant: p>5%) is observed on the linear moduli G' and G".

Figure 11:
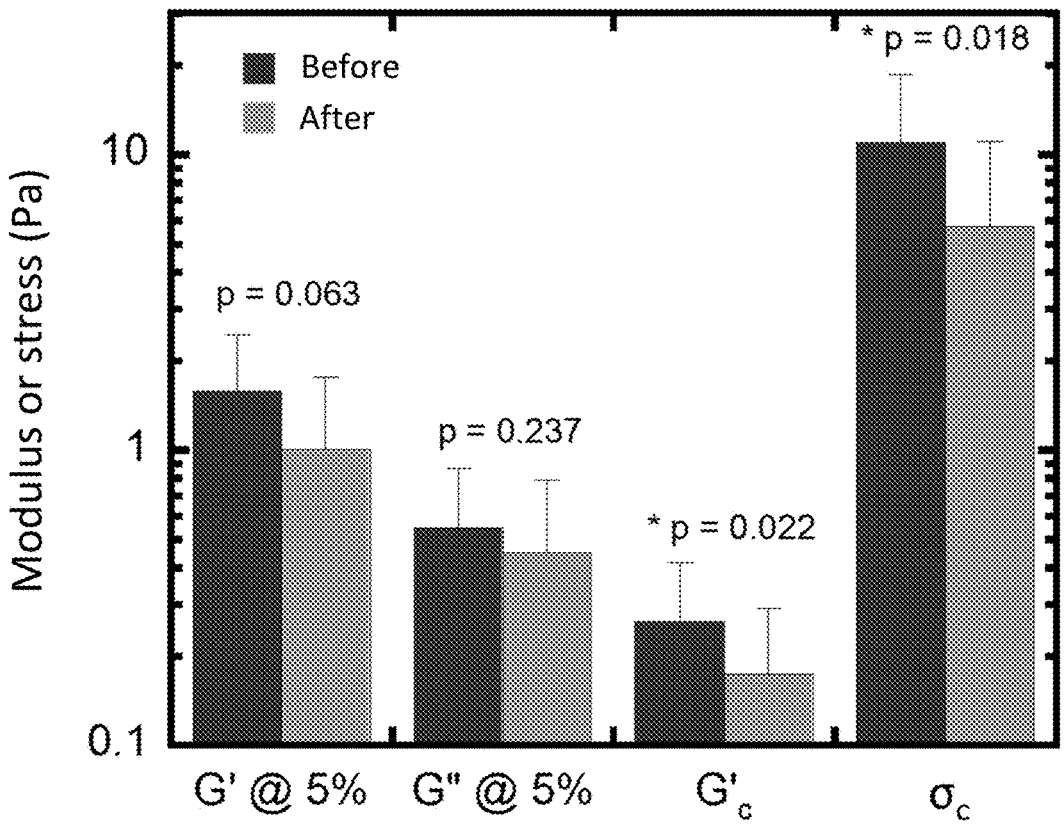
FIG. 11 is a graph showing the values of the parameters G' and G" measured at 5% deformation and the parameters $G'_c$ and $σ_c$ measured at the flow point in patients with cystic fibrosis, before (black) and after (grey) treatment with rhDNase.

A significant reduction (p<5%) is observed on the data $G'_c$ and $\tau_c$ measured at the flow point c (FIG. 11).

These data show that the prior treatment of patients with rhDNase has an effect on the rheological parameters of the mucus of the patient. This reveals for the first time that the measurement of linear and non-linear rheological parameters makes it possible to evaluate the mucolytic effect of a treatment.

TABLE 3

Data at V1 (average ± standard deviation), Repetition 1, measured or determined in healthy subjects or with cystic fibrosis, COPD or asthma.

|  | Healthy (n = 11) | Cystic fibrosis (n = 11) | COPD (n = 11) | Asthma (n = 12) |
| --- | --- | --- | --- | --- |
| G' at 5% (Pa) | 0.059 ± 0.052 | 1.493 ± 1.517 | 0.768 ± 0.971 | 0.218 ± 0.279 |
| G" at 5% (Pa) | 0.033 ± 0.028 | 0.533 ± 0.473 | 0.247 ± 0.229 | 0.087 ± 0.109 |
| G* at 5% (Pa) | 0.068 | 1.585 | 0.807 | 0.235 |
| $G_c$ (Pa) | 0.042 ± 0.027 | 0.256 ± 0.182 | 0.202 ± 0.169 | 0.064 ± 0.049 |
| $\sigma_c$ (Pa) | 1.293 ± 1.020 | 11.221 ± 7.271 | 10.574 ± 9.315 | 3.503 ± 2.762 |
| $\tau_p$ (Pa) | 0.005 ± 0.004 | 0.337 ± 0.662 | 0.076 ± 0.096 | 0.023 ± 0.035 |
| tan δ (linear domain) | 0.383 ± 0.151 | 0.272 ± 0.053 | 0.284 ± 0.092 | 0.336 ± 0.123 |
| EF (Elastic force) (Pa²) | 0.088 ± 0.109 | 187.99 ± 475.66 | 12.921 ± 24.072 | 1.584 ± 1.986 |

TABLE 4

Data at V1 (average ± standard deviation), Repetition 2, measured or determined in healthy subjects or with cystic fibrosis, COPD or asthma.

|  | Healthy (n = 11) | Cystic fibrosis (n = 11) | COPD (n = 11) | Asthma (n = 12) |
| --- | --- | --- | --- | --- |
| G' at 5% (Pa) | 0.111 ± 0.164 | 1.214 ± 2.499 | 0.610 ± 0.798 | 0.082 ± 0.118 |
| G" at 5% (Pa) | 0.062 ± 0.085 | 0.482 ± 0.959 | 0.221 ± 0.212 | 0.046 ± 0.054 |
| G* t 5% (Pa) | 0.127 | 1.306 | 0.649 | 0.094 |
| $G_c$ (Pa) | 0.045 ± 0.029 | 0.203 ± 0.139 | 0.188 ± 0.125 | 0.068 ± 0.061 |
| $\sigma_c$ (Pa) | 1.587 ± 1.735 | 8.290 ± 4.472 | 9.473 ± 7.857 | 4.768 ± 6.409 |
| $\tau_p$ (Pa) | 0.021 ± 0.042 | 16.504 ± 63.646 | 0.038 ± 0.062 | 0.007 ± 0.004 |
| tan δ (linear domain) | 0.338 ± 0.069 | 0.278 ± 0.091 | 0.321 ± 0.113 | 0.419 ± 0.117 |
| EF (Pa²) | 0.496 ± 0.867 | 7692.55 ± 27662.57 | 10.098 ± 18.834 | 1.058 ± 1.261 |

As a whole, these data show that the rheological parameters G', G", G*, $\sigma_c$ $\tau_p$, tan δ and EF, and to a lesser extent the parameters $\gamma_p$ and $\gamma_c$, make it possible to distinguish clearly and in a significant manner patients suffering from different respiratory diseases (cystic fibrosis, COPD, or asthma). These parameters may thus be used as biomarkers of respiratory and/or pulmonary diseases.

The data show for the first time that these parameters are discriminating when they are measured in the linear zone but also at the flow point c of the deformation curve. The combination of each of these parameters, measured in the linear zone but also at the flow point c of the deformation curve makes it possible to reinforce the distinction of each of these diseases as well as healthy subjects. These different parameters may thus be used for a diagnosis, a prognosis, a 2. Clinical Study No 2: Subjects with BTS, COPD or Asthma 2.1. Materials and Methods The clinical protocol was conducted by the CHU of Montpellier. Three groups of patients were retained: 24 with bronchiectasis (BTS), 14 with COPD and 10 severe asthmatic (AS).

During a single visit, all the patients expectorate spontaneously. The saliva is separated and the sample is homogenised according to the protocol described in WO/2019/020932 (Method for Processing a Sputum Sample and Method for the Rheometric Measurement of a Preprocessed Sample of This Kind).

The rheological tests are carried out at 37° C. with the Rheomuco apparatus (Rheonova, France). A sequence of oscillations at 1 Hz is applied with an increasing amplitude by steps of 0.1 to 10000% in order to extract the rheological properties of the sputum in the linear (small deformations, typically <20%) and non-linear (large deformations) domains.

2.2. Results

The data show that the moduli G', G", G*, and tan δ (damping factor), as well as the marker a, (critical stress), measured at the flow point of the deformation curve, are all selective markers, and are so in a statistically significant manner: the different pathologies are clearly discriminated (with however a COPD-BTS overlap for the markers G', G", G* and tan δ; table 5).

The parameters G', G" and G*, measured in the linear zone of the deformation curve (at 5% deformation), are particularly suitable for discriminating patients with asthma from those with COPD or BTS.

The data reveal that the parameter $\sigma_c$ is particularly discriminating, since it makes it possible to distinguish clearly subjects with COPD from those with BTS or instead from those with asthma.

Thus, the determination of a combination of at least one rheological parameter in the linear zone of the deformation curve (in particular G', G" or G*) and at least one rheological parameter in the non-linear zone of the deformation curve (in particular at the flow point, notably $\sigma_c$), makes it possible to discriminate with precision each of the 3 diseases tested (BTS, COPD, or asthma).

stratification or instead the monitoring of respiratory diseases, but also for the evaluation of the effectiveness of a treatment of these diseases.

3. Clinical Study No 3: Subjects with COPD 3.1. Materials and Methods

The clinical protocol was carried out by the University Hospital of Basle. A group of COPD patients was retained.

During a single visit, all the patients expectorate spontaneously. The saliva is separated and the sample is homogenised according to the protocol described in WO/2019/020932 (Method for Processing a Sputum Sample and Method for the Rheometric Measurement of a Preprocessed Sample of This Kind).

The rheological tests are carried out at 37° C. with the Rheomuco apparatus (Rheonova, France). A sequence of oscillations at 1 Hz is applied with an increasing amplitude by steps of 0.1 to 10000% in order to extract the rheological properties of the sputum in the linear (small deformations, typically <20%) and non-linear (large deformations) domains.

3.2. Results

The data show the moduli G', G", G*, and tan δ (damping factor), as well as the marker $\sigma_c$ (critical stress), measured at the flow point of the deformation curve; Table 6).

TABLE 5

Rheological data measured or determined in subjects with bronchiectasis (BTS), COPD or asthma (AS).

| Rheological parameter | | AS (n = 10) | COPD (n = 14) | BTS (n = 24) |
|---|---|---|---|---|
| Elastic modulus | G' (Pa) | 12.62 ± 10.06 | 3.01 ± 1.43 | 2.8 ± 1.83 |
| Viscous modulus | G" (Pa) | 2.64 ± 1.74 | 0.85 ± 0.18 | 0.87 ± 0.45 |
| Complex modulus | G* (Pa) | 12.89 ± 10.33 | 3.13 ± 1.42 | 2.93 ± 1.86 |
| Damping factor | tan δ (-) | 0.24 ± 0.06 | 0.34 ± 0.16 | 0.32 ± 0.08 |
| Critical stress | $\sigma_c$ (Pa) | 63.08 ± 62.86 | 24.1 ± 11.92 | 36.19 ± 21.4 |

Figure 12:
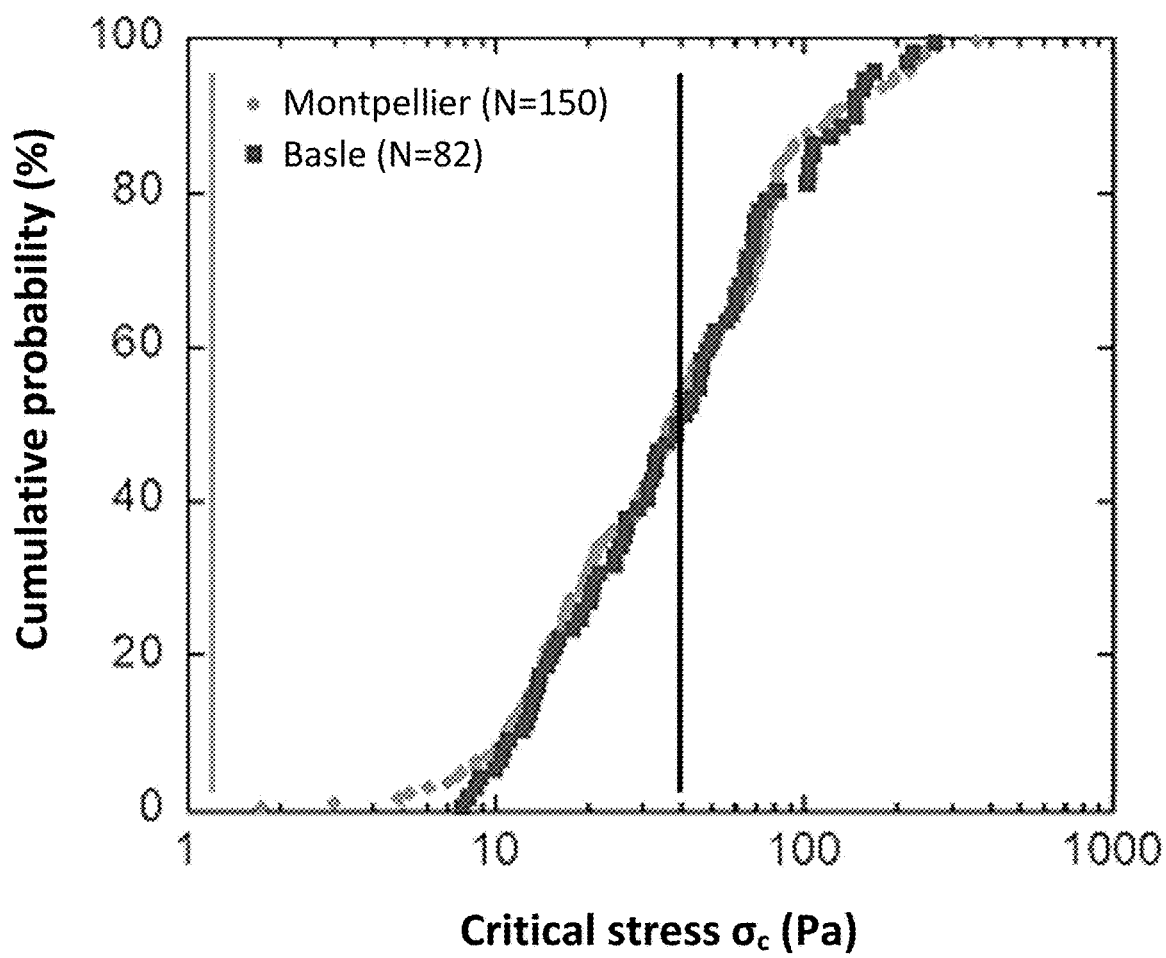
FIG. 12 is a graph showing the values of the parameter $σ_c$ measured in patients with bronchiectasis (BTS), COPD or asthma during two clinical studies no 2 and 3 (conducted respectively by the CHU of Montpellier (grey diamonds) and by Basle University Hospital (black squares), as well as the detection limit of the 3 diseases (grey line) and the detection limit of an exacerbation (black line), involving a therapeutic decision.

FIG. 12 shows the data obtained for the marker a, (critical stress), for each subject tested. The data show that detection limits can be clearly defined.

The detection limit of the 3 muco-obstructive diseases included in the study (BTS, COPD and asthma, all diseases together) lies at 1 Pa (grey line in FIG. 12): the muco-obstructive diseases are detected if $\sigma_c$>1 Pa (grey line in FIG. 12).

The detection limit of an exacerbation (BTS, COPD and asthma, all diseases together) lies at 39 Pa: an exacerbation is detected if $\sigma_c$>39 Pa (black line in FIG. 12).

As a whole, these data show that the rheological parameters G', G", G*, tan δ and $\sigma_c$, make it possible to distinguish clearly and in a significant manner patients suffering from different respiratory diseases (BTS, COPD, or asthma). These parameters may thus be used as biomarkers of respiratory and/or pulmonary diseases.

These data show for the first time that these parameters are discriminatory when they are measured in the linear zone but also at the flow point c of the deformation curve. The combination of each of these parameters, measured in the linear zone but also at the flow point c of the deformation curve makes it possible to reinforce the distinction of each of these diseases and healthy subjects. These different parameters may thus be used for a diagnosis, a prognosis, a

TABLE 6

Rheological data measured or determined in subjects with bronchiectasis (BTS), COPD or asthma (AS).

| Rheological parameter | | COPD (n = 50) |
|---|---|---|
| Elastic modulus | G' (Pa) | 4.79 ± 4.09 |
| Viscous modulus | G" (Pa) | 1.28 ± 0.78 |
| Complex modulus | G* (Pa) | 5.05 ± 4.14 |
| Damping factor | tan δ (-) | 0.29 ± 0.07 |
| Critical stress | $\sigma_c$ (Pa) | 54.1 ± 26.4 |

FIG. 12 shows the data obtained for the marker a, (critical stress), for each subject tested. The data are perfectly corroborated with the data from the CHU of Montpellier (Clinical study no 2).

The detection limit of COPD lies at 1 Pa (grey line in FIG. 12): muco-obstructive diseases are detected if $\sigma_c$>1 Pa (grey line in FIG. 12).

The detection limit of a COPD exacerbation lies at 39 Pa: an exacerbation is detected if $\sigma_c$>39 Pa (black line in FIG. 12).

4. Summary of the 3 Clinical Studies

The average values and the standard deviations for each of the rheological parameters measured or determined in the three clinical studies described above (studies no 1 to 3) were determined, for each of the diseases tested and for healthy subjects. The values obtained are shown in Tables 1 and 2 presented above, in the descriptive part of the present invention.

These data show for the first time that these parameters are discriminating when they are measured in the linear zone but also at the flow point c of the deformation curve. The combination of each of these parameters, measured in the linear zone but also at the flow point c of the deformation curve makes it possible to reinforce the distinction of each of these diseases as well as healthy subjects. These different parameters may thus be used for a diagnosis, a prognosis, a stratification or instead the monitoring of respiratory diseases, but also for the evaluation of the effectiveness of a treatment of these diseases.

Thus, the data from the three clinical studies presented above show that the determination of a combination of at least one rheological parameter in the linear zone of the deformation curve and at least one rheological parameter in the non-linear zone of the deformation curve (in particular at the flow point), makes it possible to discriminate with precision each of the 4 diseases tested (cystic fibrosis, BTS, COPD, or asthma).

The invention claimed is:

1. An in vitro method for diagnosing, stratifying, prognosing and/or monitoring a lung disease and/or a respiratory disease, comprising:
   (i) using a rheological measurement apparatus to establish a deformation curve for a sample of mucus A of a subject, the deformation curve comprising a linear zone, representing a linear deformation of the sample, and a non-linear zone, representing a non-linear deformation of the sample; wherein said sample of mucus A is placed in the rheological measurement apparatus between two slides rotationally moveable with respect to each other;
   (ii) measuring a value $A_{nl}$ of at least one first rheological parameter on said a sample of mucus A, in the non-linear zone of said deformation curve; and
   (iii) measuring a value $A_l$ of at least one second rheological parameter on said sample of mucus A, in the linear zone of said deformation curve;
   the at least one first rheological parameter measured in the non-linear zone comprises at least critical stress ($\sigma_c$), and
   the at least one second rheological parameter measured in the linear zone comprises at least one of complex modulus (G*), elasticity modulus (G'), viscosity modulus (G"), and damping factor (tan δ).

2. The method according to claim 1, wherein the two slides of the rheological measurement apparatus comprise a regular arrangement of pyramids with square base.

3. The method according to claim 1, wherein the value $A_l$ of the at least one rheological parameter is measured at a deformation less than or equal to 10%.

4. The method according claim 1, wherein the value $A_{nl}$ of the at least one rheological parameter is measured at a deformation greater than 10%.

5. The method according to claim 1, wherein the value $A_{nl}$ of the at least one rheological parameter is measured at a flow point "c" of the sample of mucus.

6. The method according to claim 1, wherein the measured value $A_l$ and/or the value $A_{nl}$ is compared with a limit value, and wherein the measured value $A_l$ and/or the value $A_{nl}$ being different than the limit value correlates to:
   (i) the subject having a lung disease and/or a respiratory disease,
   (ii) a prognosis of a lung disease and/or a respiratory disease that is negative,
   (iii) the subject having a lung disease and/or a respiratory disease that is exacerbated, or
   (iv) treatment of a lung disease and/or a respiratory disease being ineffective.

7. The method according to claim 1, further comprising measuring the value $B_l$ of at least one rheological parameter on a second sample of mucus (B) of said subject, in a linear zone of a deformation curve of the second sample; and/or measuring the value $B_{nl}$ of at least one rheological parameter on the second sample (B), in a non-linear zone of said deformation curve of the second sample; said second sample (B) having been obtained/taken after sample (A), and wherein the measured value $B_l$ being different from the measured value $A_l$ and/or the measured value $B_{nl}$ being different from the measured value $A_{nl}$ correlates to:
   (i) the subject having a lung disease and/or a respiratory disease,
   (ii) a prognosis of a lung disease and/or a respiratory disease that is negative,
   (iii) the subject having a lung disease and/or a respiratory disease that is exacerbated, or
   (iv) treatment of a lung disease and/or a respiratory disease being ineffective.

8. The method according to claim 7, further comprising the determination of an evolution $E_l$, of the value of the rheological parameter measured in the linear zone and/or an evolution $E_{nl}$ of the value of the rheological parameter measured in the non-linear zone, wherein the evolution $E_l$ is determined by comparing the value $B_l$ with the value $A_l$ and/or the evolution $E_{nl}$ is determined by comparing the value $B_{nl}$ with the value $A_{nl}$.

9. The method according to claim 8, wherein the second sample of mucus is measured after administration of a treatment of the lung disease and/or respiratory disease, and the evolution $E_l$ and/or the evolution $E_{nl}$ correlates to an evaluation of the efficacy of the treatment of the lung disease and/or the respiratory disease.

10. The method according to claim 7, wherein the value, and/or the value is/are measured using a rheological measurement apparatus in which each sample is placed between two slides rotationally moveable with respect to each other.

11. The method according to claim 1, wherein the at least one first rheological parameter measured in the non-linear zone further comprises a parameter selected from the group consisting of plastic deformation ($\gamma_p$), critical deformation ($\gamma_c$), plastic stress ($\tau_p$), flow stress threshold ($\tau_c$), and elastic force (EF).

12. The method according to claim 1, wherein the lung disease and/or the respiratory disease is selected from the group consisting of: asbestosis; sleep apnea; obstructive sleep apnoea syndrome; asphyxia; asthma; bronchiectasis; bronchitis; chronic obstructive pulmonary disease (COPD); lung cancer; bronchial cancer; pulmonary carcinoma; pulmonary tumour; whooping cough; croup; alpha1-antitrypsine deficiency; emphysema; cystic fibrosis; idiopathic pulmonary fibrosis; influenza; hantavirus pulmonary syndrome; pulmonary arterial hypertension (PAHT); lymphangioleiomyomatosis (LAM); chronic obstructive pulmonary disease (COPD); pleuritis; pneumonia; bronchopneumonia; pulmonary embolism; pulmonary oedema; pulmonary abscess; cold; sinusitis; sarcoidosis; thoracic trauma; chronic cough; tuberculosis; infection by the respiratory syncytial virus (RSV); bronchiolitis; bronchiolitis obliterans organising pneumonia (BOOP); allergy; allergic rhinitis; primary ciliary dyskinesia (PCD); bronchiectasis (BTS); pneumoconiosis; pneumothorax (PNO); pleuritis; cancer of the pleura; legionellosis; and psittacosis.

13. An in vitro method for evaluating the efficacy of a treatment of a lung disease and/or a respiratory disease, comprising:
   (i) using a rheological measurement apparatus to establish a deformation curve for a sample of mucus A of a subject, said subject suffering from the lung disease and/or the respiratory disease and having received at least one administration of said treatment, the deformation curve comprising a linear zone, representing a linear deformation of the sample, and a non-linear zone, representing a non-linear deformation of the sample; wherein said sample of mucus A is placed in the rheological measurement apparatus between two slides rotationally moveable with respect to each other;
   (ii) measuring a value $A_{nl}$ of at least one first rheological parameter on said sample of mucus A, in the non-linear zone of said deformation curve; and
   (iii) measuring a value $A_l$ of at least one second rheological parameter on said sample of mucus A, in the linear zone of said deformation curve;
   the at least one first rheological parameter measured in the non-linear zone comprises at least critical stress ($\sigma_c$), and
   the at least one second rheological parameter measured in the linear zone comprises at least one of complex modulus (G*), elasticity modulus (G'), viscosity modulus (G"), and damping factor (tan δ).

14. The method according to claim 13, wherein the at least one first rheological parameter measured in the non-linear zone further comprises a parameter selected from the group consisting of plastic deformation ($\gamma_p$), critical deformation ($\gamma_c$), plastic stress ($\tau_p$), flow stress threshold ($\tau_c$), and elastic force (EF).

15. The method according to claim 13, wherein the value $A_l$ of at least one rheological parameter is measured at a deformation less than or equal to 10%.

16. The method according claim 13, wherein the value $A_{nl}$ of at least one rheological parameter is measured at a deformation greater than 10%.

17. The method according to claim 13, wherein the value $A_{nl}$ of at least one rheological parameter is measured at a flow point "c" of the sample of mucus.

18. The method according to claim 13, further comprising comparing the measured value $A_l$ and/or the value $A_{nl}$ to a limit value, and wherein the measured value $A_l$ and/or the value $A_{nl}$ being different than the limit value correlates to the treatment of a lung disease and/or a respiratory disease being ineffective.

19. The method according to claim 13, wherein the two slides of the rheological measurement apparatus comprise a regular arrangement of pyramids with square base.

20. An in vitro method for diagnosing, stratifying, prognosing and/or monitoring a lung disease and/or a respiratory disease, comprising:
   (i) measuring a value $A_{nl}$ at least one first rheological parameter on a sample of mucus A of a subject, in a non-linear zone of a deformation curve of the sample;
   (ii) measuring a value $A_l$, of at least one second rheological parameter on said sample of mucus A, in a linear zone of said deformation curve of the sample; and
   (iii) diagnosing, stratifying, prognosing and/or monitoring a lung disease and/or a respiratory disease by comparing the measured values $A_l$ and/or $A_{nl}$ to a limit value; wherein the subject has a lung disease and/or a respiratory disease, or the prognosis of a lung disease and/or a respiratory disease is negative, or a lung disease and/or a respiratory disease is exacerbated, when at least one of the measured values $A_l$ and/or $A_{nl}$ is different from the limit value; wherein:
   the at least one first rheological parameter measured in the non-linear zone comprises at least critical stress ($\sigma_c$),
   the at least one second rheological parameter measured in the linear zone comprises at least one of complex modulus (G*), elasticity modulus (G'), viscosity modulus (G"), and damping factor (tan δ), and
   the value $A_{nl}$, and/or the value $A_l$ is/are measured using a rheological measurement apparatus in which each sample is placed between two slides rotationally moveable with respect to each other.

21. An in vitro method for evaluating the efficacy of a treatment of a lung disease and/or a respiratory disease, comprising:
   (i) measuring a value $A_{nl}$ of at least one first rheological parameter on a sample of mucus A of a subject suffering from the lung disease and/or the respiratory disease and having received at least one administration of said treatment, in a non-linear zone of a deformation curve of the sample;
   (ii) measuring a value $A_l$ of at least one second rheological parameter on said sample of mucus A, in a linear zone of said deformation curve of the sample; and
   (iii) evaluating the efficacy of a treatment of a lung disease and/or a respiratory disease by comparing the measured values $A_l$ and/or $A_{nl}$ to a limit value, wherein the treatment of a lung disease and/or a respiratory disease is ineffective, when at least one of the measured values $A_l$ and/or $A_{nl}$ is different from the limit value; wherein:
   the at least one first rheological parameter measured in the non-linear zone comprising comprises at least critical stress ($\sigma_c$),
   the at least one second rheological parameter measured in the linear zone comprises at least one of one of complex modulus (G*), elasticity modulus (G'), viscosity modulus (G"), and damping factor (tan δ), and
   the value $A_{nl}$, and/or the value $A_l$ is/are measured using a rheological measurement apparatus in which each sample is placed between two slides rotationally moveable with respect to each other.

* * * * *